(12) United States Patent
Urch et al.

(10) Patent No.: US 9,951,028 B2
(45) Date of Patent: Apr. 24, 2018

(54) AGRICULTURAL CHEMICALS

(71) Applicant: REDAG CROP PROTECTION LTD, Cheshire (GB)

(72) Inventors: Christopher Urch, Cheshire (GB); William Thompson, Cheshire (GB)

(73) Assignee: REDAG CROP PROTECTION LTD., Cheshire (GB)

( * ) Notice: Subject to any disclaimer, the term of this patent is extended or adjusted under 35 U.S.C. 154(b) by 0 days.

(21) Appl. No.: 14/917,191

(22) PCT Filed: Sep. 18, 2014

(86) PCT No.: PCT/GB2014/052845
§ 371 (c)(1),
(2) Date: Mar. 7, 2016

(87) PCT Pub. No.: WO2015/040409
PCT Pub. Date: Mar. 26, 2015

(65) Prior Publication Data
US 2016/0214945 A1 Jul. 28, 2016

(30) Foreign Application Priority Data

Sep. 18, 2013 (GB) .................................. 1316602.0

(51) Int. Cl.
| | |
|---|---|
| *C07D 239/553* | (2006.01) |
| *A01N 37/34* | (2006.01) |
| *A01N 43/54* | (2006.01) |
| *A01N 43/713* | (2006.01) |
| *C07D 239/54* | (2006.01) |
| *C07D 471/02* | (2006.01) |
| *C07D 257/04* | (2006.01) |
| *C07D 257/06* | (2006.01) |
| *C07D 271/08* | (2006.01) |
| *A01N 37/10* | (2006.01) |
| *A01N 43/653* | (2006.01) |
| *A01N 43/82* | (2006.01) |
| *A01N 43/90* | (2006.01) |

(52) U.S. Cl.
CPC ......... *C07D 239/553* (2013.01); *A01N 37/10* (2013.01); *A01N 37/34* (2013.01); *A01N 43/54* (2013.01); *A01N 43/653* (2013.01); *A01N 43/713* (2013.01); *A01N 43/82* (2013.01); *A01N 43/90* (2013.01); *C07D 239/54* (2013.01); *C07D 257/04* (2013.01); *C07D 257/06* (2013.01); *C07D 271/08* (2013.01); *C07D 471/02* (2013.01)

(58) Field of Classification Search
CPC .................................................. C07D 239/553
USPC ....................................................... 504/243
See application file for complete search history.

(56) References Cited

U.S. PATENT DOCUMENTS

| | | | |
|---|---|---|---|
| 6,534,037 B1 | 3/2003 | Kasina et al. | |
| 9,084,425 B2 | 7/2015 | Mosrin et al. | |
| 2002/0045550 A1* | 4/2002 | Carlsen ................. | A01N 41/02 504/242 |
| 2012/0302444 A1* | 11/2012 | Kolb ...................... | A01N 43/54 504/243 |

FOREIGN PATENT DOCUMENTS

| | | |
|---|---|---|
| EP | 2474226 A1 | 7/2012 |
| JP | H04182462 A | 6/1992 |
| WO | WO 1997002253 A1 | 1/1997 |
| WO | WO 1997045418 A1 | 12/1997 |
| WO | 01/83459 A2 | 11/2001 |

(Continued)

OTHER PUBLICATIONS

Search Report under Section 17(5) issued in a corresponding United Kingdom Patent Application No. GB1316602.0 dated Feb. 28, 2014.

(Continued)

*Primary Examiner* — Johann R Richter
(74) *Attorney, Agent, or Firm* — Morgan, Lewis & Bockius LLP

(57) ABSTRACT

The present invention relates to compounds which are of use in the field of agriculture as herbicides. The invention also relates to compositions comprising said compounds and methods of using said compounds.

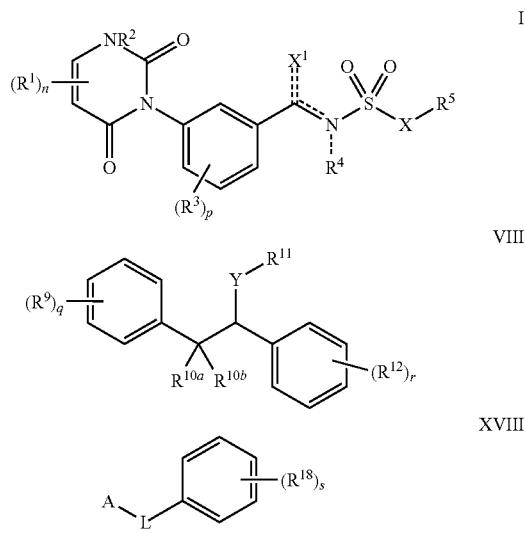

15 Claims, No Drawings

(56) References Cited

FOREIGN PATENT DOCUMENTS

| WO | WO 2001083459 A2 | 11/2001 |
| WO | 2011/064533 A2 | 6/2011 |
| WO | 2013/010882 A | 1/2013 |
| WO | WO 2013010882 A2 | 1/2013 |

OTHER PUBLICATIONS

Search Report under Section 17(8) issued in a corresponding United Kingdom Patent Application No. GB1316602.0 dated Aug. 26, 2014.
Seo et al., "Enantioselective organocatalytic Michael addition of 2-arylacetates and 2-arylacetonitriles having an electron-withdrawing group to α,β-unsaturated aldehydes," Tetrahedron Letters, 53(23): 2809-2812 (2012).
Miocque et al., "Obtention d'azacyclenes par heterocyclisation d'alcynylformamides en milie acide," Bulletin de la Societe Chimique de France, (11-12, Pt. 2), 1237-1240 (1977).
PCT/GB2014/052845 International Search Report and Written Opinion, dated May 8, 2015.

\* cited by examiner

AGRICULTURAL CHEMICALS

This application is the U.S. national stage application of International (PCT) Patent Application Serial No. PCT/GB2014/052845, filed Sep. 18, 2014, which claims the benefit of GB Application No. 1316602.0, filed Sep. 18, 2013. The entire disclosure of each of these applications is hereby incorporated by reference.

The present invention relates to compounds which are of use in the field of agriculture as herbicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in USA and strobilurin-resistant strains of septoria fungal species.

Recent research also suggests that the geographical spread of many crop pests and diseases is increasing, possibly as a result of global warming.

An aim of the present invention is to provide pesticides (e.g. herbicides) which have activity either non-selectively, i.e. broad spectrum activity, or which are active specifically against selective target organisms.

An aim of the present invention is to provide compounds which are less persistent in the environment after use than prior art compounds.

Alternatively or additionally the compounds of the present invention are less prone to bioaccumulation once in the food chain than prior art compounds.

Another aim of the invention is to provide compounds which are less harmful to humans than prior art compounds.

Alternatively or additionally, the compounds of the invention may be less harmful than prior art compounds to one or more of the following groups: amphibians, fish, mammals (including domesticated animals such as dogs, cats, cows, sheep, pigs, goats, etc), reptiles, birds, and beneficial invertebrates (e.g. bees and other insects, or worms), beneficial nematodes, beneficial fungi and nitrogen-fixing bacteria.

The compounds of the invention may be as active or more active than prior art compounds. They may have activity against organisms which have developed a resistance to prior art compounds. However, the present invention also concerns compounds which have a lower level of activity relative to that of prior art compounds. These lower activity compounds are still effective as herbicides but have other advantages relative to existing compounds such as, for example, a reduced environmental impact.

The compounds of the invention may be more selective than the parent, i.e. they may have better, similar or even slightly lower activity than prior art compounds against target species but have a significantly lower activity against non-target species (e.g. the crops which are being protected).

This invention provides compounds that achieve one or more of the above aims. The compounds may be active in their own right or may metabolise or react in aqueous media to yield an active compound.

SUMMARY OF THE INVENTION

Pyrimidones

In a first aspect of the invention is provided a compound of formula I:

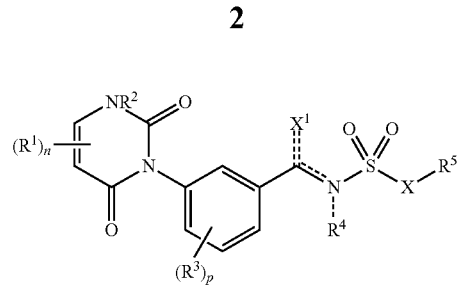

wherein
----- represents a single bond or a double bond;
X is independently $NR^6$ or $CR^7R^7$;
====== $X^1$ is selected from: =O, —$R^7$ or (—$R^7$)$_2$; with the proviso that if ====== $X^1$ is =O, X is $CR^7R^7$;
$R^1$ and $R^3$ are each independently at each occurrence selected from $C_1$-$C_4$ alkyl, $C_1$-$C_4$-haloalkyl, halogen, nitro, $OR^8$, $SR^8$, cyano, $C_2$-$C_4$ alkenyl, $C_2$-$C_4$ alkynyl, $C_3$-$C_6$ cycloalkyl and $NR^8R^8$;
$R^2$ and $R^6$ are each independently selected from: H, $C_1$-$C_4$ alkyl, $C_3$-$C_6$-cycloalkyl and $C_1$-$C_4$ haloalkyl;
$R^4$ is absent or is independently selected from: H, $C_1$-$C_4$ alkyl, $C_3$-$C_6$-cycloalkyl and $C_1$-$C_4$ haloalkyl;
$R^5$ is independently selected from $C_1$-$C_4$ alkyl, $C_3$-$C_6$-cycloalkyl and $C_1$-$C_4$ haloalkyl;
$R^7$ is independently at each occurrence selected from: H, $C_1$-$C_4$ alkyl, $C_3$-$C_6$-cycloalkyl and $C_1$-$C_4$ haloalkyl;
$R^8$ is independently at each occurrence selected from; H, $C_1$-$C_4$ alkyl, C(O)—$C_1$-$C_4$-alkyl and $C_1$-$C_4$ haloalkyl;
n is an integer selected from 0, 1 and 2;
p is an integer independently selected from 0, 1, 2 and 3;
wherein in any $R^1$-$R^8$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;
wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;
or an agronomically acceptable salt or N-oxide thereof.

For the absence of doubt, to satisfy valency requirements, when ====== is a double bond, $R^4$ is absent. Thus, ------ may represent a single bond or be absent. Likewise, when ====== represents a double bond, ====== $X^1$ is —$R^7$ and when ====== is a single bond, ====== $X^1$ is selected from =O and (—$R^7$)$_2$.

The compound may be a compound of formula Ia:

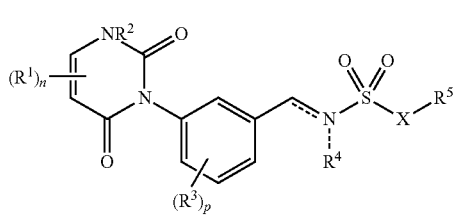

wherein

------ represents a single bond or a double bond;

X is independently $NR^6$ or $CR^7R^7$;

$R^1$ and $R^3$ are each independently at each occurrence selected from $C_1$-$C_4$ alkyl, $C_1$-$C_4$-haloalkyl, halogen, nitro, $OR^8$, $SR^8$, cyano, $C_2$-$C_4$ alkenyl, $C_2$-$C_4$ alkynyl, $C_3$-$C_6$ cycloalkyl and $NR^8R^8$;

$R^2$ and $R^6$ are each independently selected from: H, $C_1$-$C_4$ alkyl, $C_3$-$C_6$-cycloalkyl and $C_1$-$C_4$ haloalkyl;

$R^4$ is absent or is independently selected from: H, $C_1$-$C_4$ alkyl, $C_3$-$C_6$-cycloalkyl and $C_1$-$C_4$ haloalkyl;

$R^5$ is independently selected from $C_1$-$C_4$ alkyl, $C_3$-$C_6$-cycloalkyl and $C_1$-$C_4$ haloalkyl;

$R^7$ is independently at each occurrence selected from: H, $C_1$-$C_4$ alkyl, $C_3$-$C_6$-cycloalkyl and $C_1$-$C_4$ haloalkyl;

$R^8$ is independently at each occurrence selected from; H, $C_1$-$C_4$ alkyl, $C(O)$—$C_1$-$C_4$-alkyl and $C_1$-$C_4$ haloalkyl;

n is an integer selected from 0, 1 and 2;

p is an integer independently selected from 0, 1, 2 and 3;

wherein in any $R^1$-$R^8$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof.

In an embodiment, the compound of formula I or formula Ia is a compound of formula II:

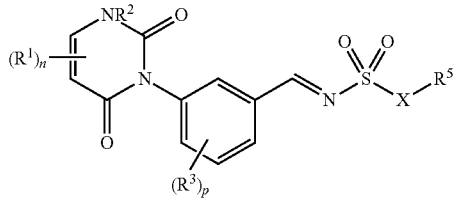

II wherein $R^1$, $R^2$, $R^3$, $R^5$, X, n and p are as described above for compounds of formula I or formula Ia.

In an embodiment, the compound of formula I or formula Ia is a compound of formula III:

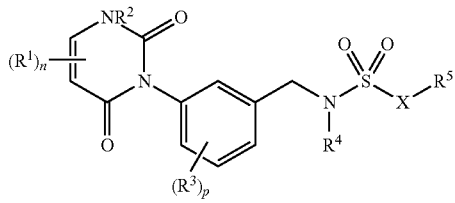

III wherein $R^1$, $R^2$, $R^3$, $R^5$, X, n and p are as described above for compounds of formula I or formula Ia and wherein $R^4$ is independently selected from: H, $C_1$-$C_4$ alkyl, $C_3$-$C_6$-cycloalkyl and $C_1$-$C_4$ haloalkyl.

In an embodiment, the compound of formula I or formula Ia is a compound of formula IV:

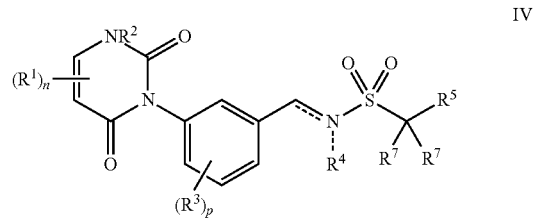

IV wherein ------, $R^1$, $R^2$, $R^3$, $R^4$, $R^5$, $R^7$, n and p are as described above for compounds of formula I or formula Ia.

In an embodiment, the compound of formula I or formula Ia is a compound of formula V:

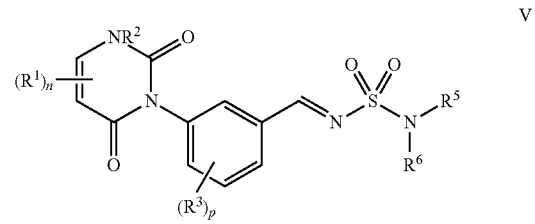

V wherein $R^1$, $R^2$, $R^3$, $R^5$, $R^6$, n and p are as described above for compounds of formula I or formula Ia.

In an embodiment, the compound of formula I or formula Ia is a compound of formula VI:

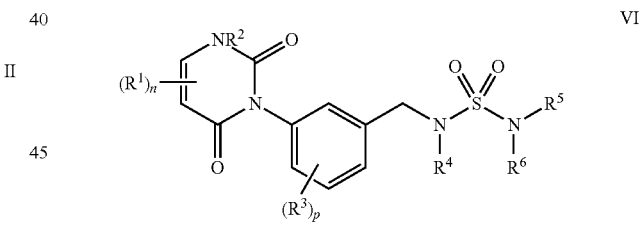

VI wherein $R^1$, $R^2$, $R^3$, $R^5$, $R^6$, n and p are as described above for compounds of formula I or formula Ia and wherein $R^4$ is independently selected from: H, $C_1$-$C_4$ alkyl, $C_3$-$C_6$-cycloalkyl and $C_1$-$C_4$ haloalkyl.

In an embodiment, the compound of formula I or formula Ia is a compound of formula VII:

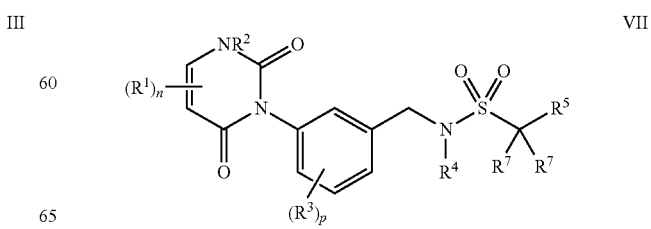

VII wherein $R^1$, $R^2$, $R^3$, $R^5$, $R^7$, n and p are as described above for compounds of formula I or formula Ia and wherein $R^4$ is independently selected from: H, $C_1$-$C_4$ alkyl, $C_3$-$C_6$-cycloalkyl and $C_1$-$C_4$ haloalkyl.

In an embodiment, the compound of formula I is a compound of formula XXIX:

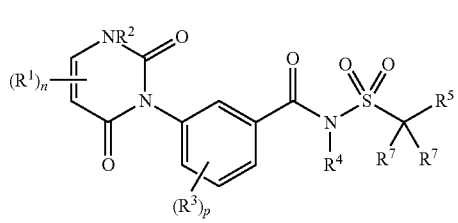

XXIX wherein $R^1$, $R^2$, $R^3$, $R^5$, $R^7$, n and p are as described above for compounds of formula I and wherein $R^4$ is independently selected from: H, $C_1$-$C_4$ alkyl, $C_3$-$C_6$-cycloalkyl and $C_1$-$C_4$ haloalkyl.

The following embodiments apply to compounds of any of formulae (I)-(VIII) and (XXIX) (including formula Ia). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

In an embodiment, ====== represents a single bond. In another embodiment, ====== represents a double bond.

In an embodiment, X is $NR^6$. Preferably $R^6$ is $C_1$-$C_4$ alkyl, e.g. methyl. Thus, X may be NMe.

In another embodiment, X is $CR^7R^7$. It may be that $R^7$ is at one occurrence H. It may be that $R^7$ is at one occurrence independently selected from $C_1$-$C_4$ alkyl, $C_3$-$C_6$-cycloalkyl and $C_1$-$C_4$ haloalkyl. Thus, it may be that $R^7$ is at one occurrence H and at the other occurrence independently selected from $C_1$-$C_4$ alkyl, $C_3$-$C_6$-cycloalkyl and $C_1$-$C_4$ haloalkyl. Preferably, $R^7$ is at one occurrence H and at the other occurrence $C_1$-$C_4$ alkyl, e.g. methyl. Thus, X may be CHMe.

====== $X^1$ may be =O. ====== $X^1$ may be —$R^7$, e.g. H. ====== $X^1$ may be (—$R^7$)$_2$, e.g. (—H)$_2$.

In an embodiment, n is 1. In another embodiment, $R^1$ is independently selected from: $C_1$-$C_4$ alkyl, $C_1$-$C_4$-haloalkyl, halogen and $C_3$-$C_6$ cycloalkyl. Thus, $R^1$ may be $C_1$-$C_4$-haloalkyl, e.g. $CF_3$.

In an embodiment, $R^3$ is independently selected from: $C_1$-$C_4$ alkyl, $C_1$-$C_4$-haloalkyl, halogen and $C_3$-$C_6$ cycloalkyl. It may be that $R^3$ is at each occurrence halogen. Said halogen substituents may be the same or different. If, for example, p is 2, $R^3$ may be at both occurrences F. As another example, if p is 2, $R^3$ may be at one occurrence Cl and at the other occurrence F.

In an embodiment, $R^2$ is independently selected from: $C_1$-$C_4$ alkyl, $C_3$-$C_6$-cycloalkyl and $C_1$-$C_4$ haloalkyl. Thus, $R^2$ may be $C_1$-$C_4$ alkyl. Preferably, $R^2$ is methyl.

$R^4$ is present when ====== represents a single bond and absent when ====== represents a double bond. When present, $R^4$ is preferably H.

In an embodiment, $R^5$ is $C_1$-$C_4$ alkyl, e.g. propyl (i.e. n-propyl or isopropyl). Most preferably, $R^5$ is isopropyl.

1,2-Diphenyl Ethyl Compounds

In a second aspect of the invention is provided a compound of formula VIII:

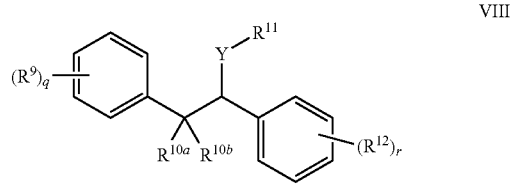

VIII wherein Y is independently selected from O, $NR^{13}$ and $CR^{14}R^{14}$;

$R^9$ and $R^{12}$ are each independently at each occurrence selected from $C_1$-$C_4$ alkyl, $C_1$-$C_4$-haloalkyl, halogen, nitro, $OR^{15}$, $SR^{15}$, cyano, $C_2$-$C_4$ alkenyl, $C_2$-$C_4$ alkynyl, $C_3$-$C_6$ cycloalkyl and $NR^{15}R^{15}$;

$R^{10a}$ is independently selected from CN and —C≡C—$R^{10c}$;

$R^{10b}$ is independently selected from: H, $C_1$-$C_4$ alkyl and $C_1$-$C_4$ haloalkyl;

$R^{10c}$ is independently selected from H and $C_1$-$C_2$-alkyl;

$R^{11}$ is selected from H, $OR^{16a}$, $C(O)R^{16a}$, $CO_2$—$R^{16b}$, $CH_2$—O—$R^{16b}$, $S(O)OR^{16b}$, $SO_3R^{16b}$ and $P(O)(OR^{16b})_2$; with the proviso that if Y is $CR^{14}R^{14}$ and $R^{10}$ is CN, $R^{11}$ is not $CO_2R^{16b}$;

$R^{13}$, $R^{14}$ and $R^{16b}$ are each independently at each occurrence selected from: H, $C_1$-$C_4$ alkyl, $C_3$-$C_6$-cycloalkyl and $C_1$-$C_4$ haloalkyl;

$R^{16a}$ is independently selected from: unsubstituted $C_1$-$C_4$ alkyl, $C_3$-$C_6$-cycloalkyl and unsubstituted $C_1$-$C_4$ haloalkyl;

$R^{15}$ is independently at each occurrence selected from; H, $C_1$-$C_4$ alkyl, C(O)—$C_1$-$C_4$-alkyl and $C_1$-$C_4$ haloalkyl;

q and r are each independently an integer selected from 0, 1, 2, 3, 4 and 5;

wherein in any $R^9$-$R^{15}$, $R^{16a}$ or $R^{16b}$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$, $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof, with the proviso that the compound is not

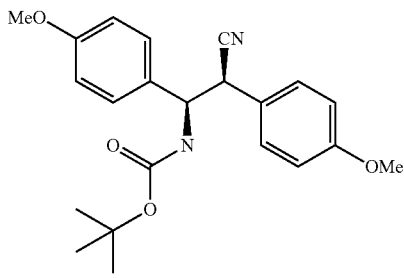

The compound may be a compound of formula VIIIa:

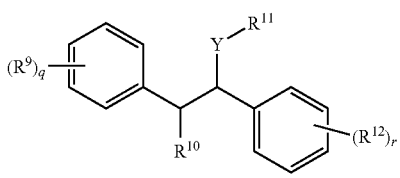

VIIIa wherein Y is independently selected from O, $NR^{13}$ and $CR^{14}R^{14}$;

$R^9$ and $R^{12}$ are each independently at each occurrence selected from $C_1$-$C_4$ alkyl, $C_1$-$C_4$-haloalkyl, halogen, nitro, $OR^{15}$, $SR^{15}$, cyano, $C_2$-$C_4$ alkenyl, $C_2$-$C_4$ alkynyl, $C_3$-$C_6$ cycloalkyl and $NR^{15}R^{15}$;

$R^{10}$ is independently selected from CN and $C_2$-$C_4$-alkynyl;

$R^{11}$ is independently selected from $C(O)R^{16}$, $CO_2$—$R^{16}$, $CH_2$—O—$R^{16}$, $S(O)OR^{16}$, $SO_3R^{16}$ and $P(O)(OR^{16})_2$; with the proviso that if Y is $CR^{14}R^{14}$ and $R^{10}$ is CN, $R^{11}$ is not $CO_2R^{16}$;

$R^{13}$, $R^{14}$ and $R^{16}$ are each independently at each occurrence selected from: H, $C_1$-$C_4$ alkyl, $C_3$-$C_6$-cycloalkyl and $C_1$-$C_4$ haloalkyl;

$R^{15}$ is independently at each occurrence selected from; H, $C_1$-$C_4$ alkyl, $C(O)$—$C_1$-$C_4$-alkyl and $C_1$-$C_4$ haloalkyl;

q and r are each independently an integer selected from 0, 1, 2, 3, 4 and 5;

wherein in any $R^9$-$R^{16}$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof.

In an embodiment, the compound of formula VIII or formula VIIIa is a compound of formula IX:

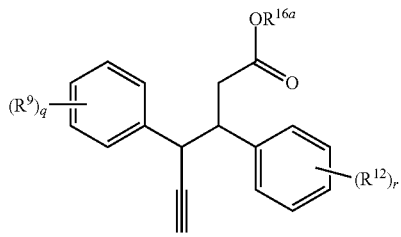

IX wherein $R^9$, $R^{12}$, $R^{16a}$, q and r are as described above for compounds of formula VIII or formula VIIIa.

In an embodiment, the compound of formula VIII is a compound of formula X:

X wherein $R^9$, $R^{12}$, $R^{16b}$, q and r are as described above for compounds of formula VIII.

In an embodiment, the compound of formula VIIIa is a compound of formula Xa:

Xa wherein $R^9$, $R^{12}$, $R^{16}$, q and r are as described above for compounds of formula VIIIa.

In an embodiment, the compound of formula VIII or formula VIIIa is a compound of formula XI:

XI wherein $R^9$, $R^{12}$, $R^{16a}$, q and r are as described above for compounds of formula VIII or formula VIIIa.

In an embodiment, the compound of formula VIII or formula VIIIa is a compound of formula XII:

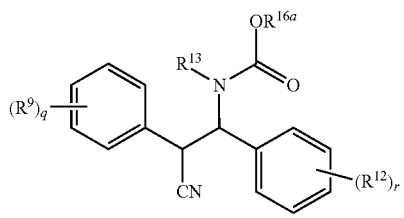

XII wherein $R^9$, $R^{12}$, $R^{13}$, $R^{16a}$, q and r are as described above for compounds of formula VIII or formula VIIIa.

In an embodiment, the compound of formula VIII or formula VIIIa is a compound of formula XIII:

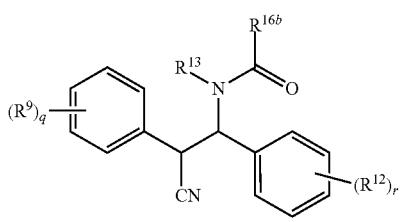

XIII wherein $R^9$, $R^{12}$, $R^{13}$, $R^{16b}$, q and r are as described above for compounds of formula VIII or formula VIIIa.

In an embodiment, the compound of formula VIII or formula VIIIa is a compound of formula XIV:

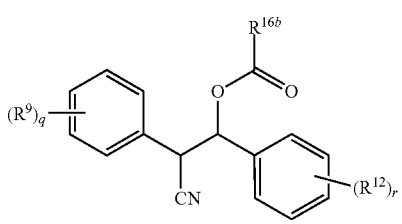

XIV wherein $R^9$, $R^{12}$, $R^{13}$, $R^{16b}$, q and r are as described above for compounds of formula VIII or formula VIIIa.

In an embodiment, the compound of formula VIII or formula VIIIa is a compound of formula XV:

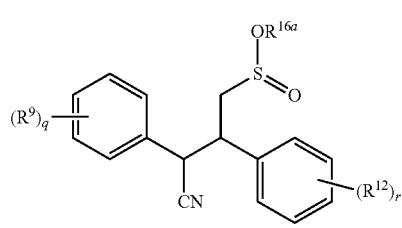

XV wherein $R^9$, $R^{12}$, $R^{16a}$, q and r are as described above for compounds of formula VIII or formula VIIIa.

In an embodiment, the compound of formula VIII or formula VIIIa is a compound of formula XVI:

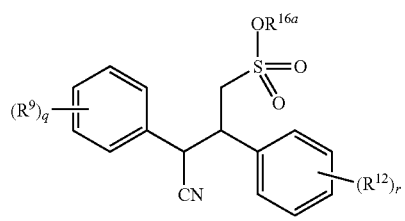

XVI wherein $R^9$, $R^{12}$, $R^{16a}$, q and r are as described above for compounds of formula VIII or formula VIIIa.

In an embodiment, the compound of formula VIII or formula VIIIa is a compound of formula XVII:

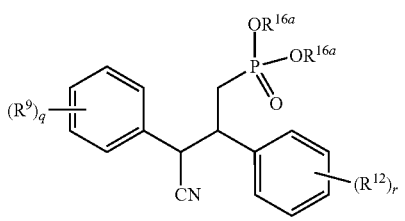

XVII wherein $R^9$, $R^{12}$, $R^{16a}$, q and r are as described above for compounds of formula VIII or formula VIIIa.

The following embodiments apply to compounds of any of formulae (VIII)-(XVII) (including formulae VIIIa and Xa). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

In an embodiment, q is 1. Where q is 1 it may be that the single $R^9$ is at the 4-position on the phenyl ring (with the rest of the molecule being at the 1 position). In an embodiment, $R^9$ is selected from is independently selected from: $C_1$-$C_4$ alkyl, $C_1$-$C_4$-haloalkyl, halogen and $C_3$-$C_6$ cycloalkyl. In an embodiment, $R^9$ is halogen, e.g. fluoro. Thus, $R^9$ may be a halogen (e.g. fluoro) at the 4-position on the phenyl ring (with the rest of the molecule being at the 1 position).

In an embodiment, r is 4. In an embodiment, $R^{12}$ is independently selected from: $C_1$-$C_4$ alkyl, $C_1$-$C_4$-haloalkyl, halogen and $C_3$-$C_6$ cycloalkyl. It may be that $R^{12}$ is at each occurrence halogen. Said halogen substituents may be the same or different. If, for example, r is 2 or 4, $R^{12}$ may be at all occurrences F. As another example, if r is 4, $R^3$ may be at one occurrence Cl and at the other three occurrences F. In a specific embodiment, the phenyl ring to which the $R^{12}$ groups are attached is

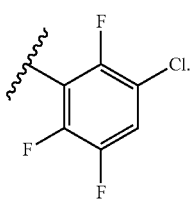 [SMILES: *c1c(F)c(F)cc(Cl)c1F]

In another specific embodiment, the phenyl ring to which the $R^{12}$ groups are attached is

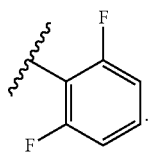

In an embodiment, $R^{10}$ is CN. In an alternative embodiment, $R^{10}$ is $C_2$-$C_4$-alkynyl, e.g. ethynyl.

In an embodiment, $R^{10a}$ is CN. In an alternative embodiment, $R^{10a}$ is —C≡C—$R^{10c}$. Preferably, $R^{10a}$ is ethynyl (i.e. —C≡C—H).

$R^{10b}$ is independently selected from: H, $C_1$-$C_4$ alkyl and $C_1$-$C_4$ haloalkyl. $R^{10b}$ may be selected from H, Me and $CF_3$. $R^{10b}$ may be Me. Preferably, $R^{10b}$ is H.

In an embodiment, Y is O. Preferably, however, Y is not O. Thus, Y may be selected from $NR^{13}$ and $CR^{14}R^{14}$.

In another embodiment, Y is $NR^{13}$. $R^{13}$ is preferably H. Thus Y may be NH. In yet another embodiment, Y is $CR^{14}R^{14}$. $R^{14}$ is preferably at each occurrence H. Thus, Y may be $CH_2$.

$R^{11}$ may be selected from $C(O)R^{16a}$, $CO_2$—$R^{16b}$, $CH_2$—O—$R^{16b}$, $S(O)OR^{16b}$, $SO_3R^{16b}$ and $P(O)(OR^{16b})_2$.

In an embodiment, $R^{11}$ is $C(O)R^{16}$. In an alternative embodiment. $R^{11}$ may be $CH_2$—O—$R^{16}$. In these embodiments, $R^{16}$ is preferably $C_1$-$C_4$ alkyl, e.g. methyl.

In further embodiments, $R^{11}$ is $S(O)OR^{16}$ or $R^{11}$ is $SO_3R^{16}$ or $R^{11}$ is $P(O)(OR^{16})_2$. In these embodiments, $R^{16}$ is preferably H.

Alternatively, $R^{11}$ may be $CO_2$—$R^{16}$. In this embodiment, $R^{16}$ may be independently selected from H or $C_1$-$C_4$ alkyl. Thus, $R^{11}$ may be $CO_2H$ or $R^{11}$ may be $CO_2Me$.

Furazans, Tetrazoles and 1,2,4-Triazoles

In a third aspect of the invention is provided a compound of formula XVIII:

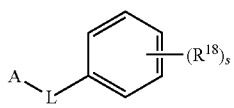

XVIII wherein A is independently selected from a furazan, a tetrazole and a 1,2,4-triazole L is independently selected from: —$NR^{19}$—$CH_2$—, —O—N=CH—, —N=CH— and —$NR^{19}SO_2$—;

$R^{18}$ is independently at each occurrence selected from $C_1$-$C_4$ alkyl, $C_1$-$C_4$-haloalkyl, halogen, nitro, $OR^{20}$, $SR^{20}$, $SO_2R^{20}$, cyano, $C_2$-$C_4$ alkenyl, $C_2$-$C_4$ alkynyl, $C_3$-$C_6$ cycloalkyl and $NR^{20}R^{20}$;

$R^{19}$ is independently selected from H, $C_1$-$C_4$ alkyl, $C_3$-$C_6$-cycloalkyl and $C_1$-$C_4$ haloalkyl;

$R^{20}$ is independently at each occurrence selected from H, $C_1$-$C_4$ alkyl, C(O)—$C_1$-$C_4$-alkyl and $C_1$-$C_4$ haloalkyl;

s is an integer independently selected from 0, 1, 2, 3, 4 and 5;

wherein in any $R^{17}$-$R^{20}$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof.

Where L is described as —$NR^{19}$—$CH_2$—, it is intended that the nitrogen atom of the $NR^{19}$ portion of L is directly bonded to A and the carbon atom of the $CH_2$ portion of L is directly bonded to the phenyl ring of the compounds of the invention. Likewise, where L is described as —O—N=CH—, it is intended that the oxygen atom of the —O—N portion of L is directly bonded to A and the carbon atom of the CH portion of L is directly bonded to the phenyl ring of the compounds of the invention. Likewise, where L is described as —N=CH—, it is intended that the nitrogen atom of L is directly bonded to A and the carbon atom of the CH portion of L is directly bonded to the phenyl ring of the compounds of the invention. Likewise, where L is described as —$NR^{19}SO_2$—, it is intended that the nitrogen atom of the $NR^{19}$ portion of L is directly bonded to A and the sulfur atom of the $S(O)_2$ portion of L is directly bonded to the phenyl ring of the compounds of the invention.

In an embodiment, the compound of formula XVIII is a compound of formula XIX:

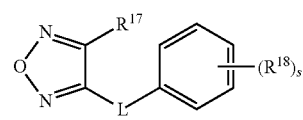

XIX wherein L, $R^{18}$ and s are as described above for compounds of formula XVIII and wherein $R^{17}$ is independently at each occurrence selected from $C_1$-$C_4$ alkyl, $C_1$-$C_4$-haloalkyl, halogen, nitro, $OR^{20}$, $SR^{20}$, $SO_2R^{20}$, cyano, $C_2$-$C_4$ alkenyl, $C_2$-$C_4$ alkynyl, $C_3$-$C_6$ cycloalkyl and $NR^{20}R^{20}$.

In an embodiment, the compound of formula XVIII is a compound of formula XX:

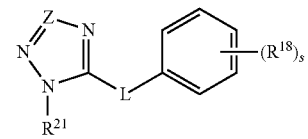

XX wherein L, $R^{18}$ and s are as described above for compounds of formula XVIII and wherein Z is independently selected from N and $CR^{17}$; $R^{17}$ is independently at each occurrence selected from $C_1$-$C_4$ alkyl, $C_1$-$C_4$-haloalkyl, halogen, nitro, $OR^{20}$, $SR^{20}$, $SO_2R^{20}$, cyano, $C_2$-$C_4$ alkenyl, $C_2$-$C_4$ alkynyl, $C_3$-$C_6$ cycloalkyl and $NR^{20}R^{20}$; and $R^{21}$ is independently selected from H, $C_1$-$C_4$ alkyl, $C_3$-$C_6$-cycloalkyl and $C_1$-$C_4$ haloalkyl.

Bicyclic Heteroaryl Compounds

In a fourth aspect of the invention is provided a compound of formula XXI:

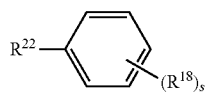

wherein
$R^{22}$ is independently selected from

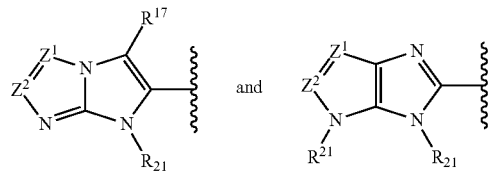

$Z^1$ and $Z^2$ are each independently selected from N and $CR^{17}$;

$R^{17}$ and $R^{18}$ are each independently at each occurrence selected from $C_1$-$C_4$ alkyl, $C_1$-$C_4$-haloalkyl, halogen, nitro, $OR^{20}$, $SR^{20}$, $SO_2R^{20}$, cyano, $C_2$-$C_4$ alkenyl, $C_2$-$C_4$ alkynyl, $C_3$-$C_6$ cycloalkyl and $NR^{20}R^{20}$;

$R^{20}$ is independently at each occurrence selected from H, $C_1$-$C_4$ alkyl, $C(O)$—$C_1$-$C_4$-alkyl and $C_1$-$C_4$ haloalkyl;

$R^{21}$ is independently at each occurrence selected from H, $C_1$-$C_4$ alkyl, $C_3$-$C_6$-cycloalkyl and $C_1$-$C_4$ haloalkyl;

s is an integer independently selected from 0, 1, 2, 3, 4 and 5;

wherein in any $R^{17}$-$R^{21}$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; =$NR^a$; =$NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof.

The compounds described in the third and fourth aspects of the invention are related. Thus, where designations (e.g. $R^{18}$) are shared across both aspects, the groups those designations represent have the same definitions.

In an embodiment, the compound of formula XVIII is a compound of formula XXII:

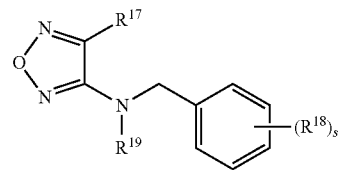

wherein $R^{18}$, $R^{19}$ and s are as described above for compounds of formula XVIII and wherein $R^{17}$ is as described above for compounds of formula XIX.

In an embodiment, the compound of formula XVIII is a compound of formula XXIII:

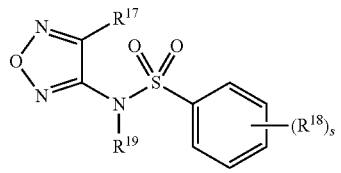

wherein $R^{18}$, $R^{19}$ and s are as described above for compounds of formula XVIII and wherein $R^{17}$ is as described above for compounds of formula XIX.

In an embodiment, the compound of formula XVIII is a compound of formula XXIV:

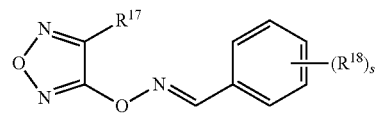

wherein $R^{18}$ and s are as described above for compounds of formula XVIII and wherein $R^{17}$ is as described above for compounds of formula XIX.

In an embodiment, the compound of formula XXII is a compound of formula XXV:

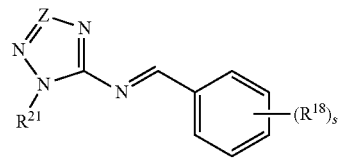

wherein $R^{18}$, and s are as described above for compounds of formula XXII and wherein Z and $R^{21}$ are as described above for compounds of formula XX.

In an embodiment, the compound of formula XXII is a compound of formula XXVI:

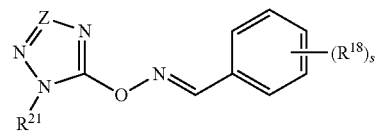

wherein $R^{18}$ and s are as described above for compounds of formula XXII and wherein Z and $R^{21}$ are as described above for compounds of formula XX.

In an embodiment, the compound of formula XXI is a compound of formula XXVII:

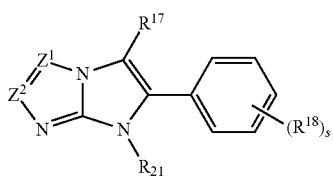

XXVII wherein $Z^1$, $Z^2$, $R^{17}$, $R^{18}$, $R^{21}$ and s are as described above for compounds of formula XXI.

In an embodiment, the compound of formula XXI is a compound of formula XXVIII:

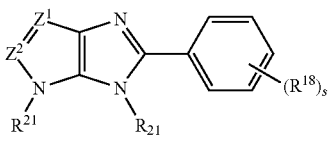

XXVIII

The following embodiments apply to compounds of any of formulae (XVIII)-(XXVIII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

In an embodiment, $R^{17}$ is independently selected from: H, $C_1$-$C_4$ alkyl, $C_1$-$C_4$-haloalkyl, halogen and $C_3$-$C_6$ cycloalkyl. Thus, $R^{17}$ may be independently selected from $C_1$-$C_4$ alkyl, $C_1$-$C_4$-haloalkyl, halogen and $C_3$-$C_6$ cycloalkyl. In a specific embodiment, $R^{17}$ is $C_1$-$C_4$ alkyl; preferably, $R^{17}$ is methyl. In another specific embodiment, $R^{17}$ is at each occurrence H.

In an embodiment, $R^{18}$ is independently at each occurrence selected from: $C_1$-$C_4$ alkyl, $C_1$-$C_4$-haloalkyl, halogen, $SO_2R^{20}$ and $C_3$-$C_6$ cycloalkyl. It may be that at one occurrence $R^{18}$ is $C_1$-$C_4$ alkyl, e.g. methyl. It may be that at one or more occurrences $R^{18}$ is $SO_2R^{20}$, e.g. $SO_2Me$. It may be that at one occurrence $R^{18}$ is $C_1$-$C_4$ haloalkyl, e.g. $CF_3$. It may also be that at one occurrence $R^{18}$ is halo. In an embodiment, s is 3. In a specific embodiment, s is 3 and $R^{18}$ represents respectively, a $C_1$-$C_4$ alkyl (e.g. methyl) group, a $SO_2R^{20}$ (e.g. $SO_2Me$) group and a $C_1$-$C_4$ haloalkyl (e.g. $CF_3$) group. Alternatively, s is 3 and $R^{18}$ represents at one occurrence a $C_1$-$C_4$ alkyl (e.g. methyl) group and at the other two occurrences a $SO_2R^{20}$ (e.g. $SO_2Me$) group. In another embodiment, s is 2. In a specific embodiment, s is 2 and $R^{18}$ represents respectively a halogen (e.g. Cl) group and a $SO_2R^{20}$ (e.g. $SO_2Me$).

In a specific embodiment, the phenyl ring to which the $R^{18}$ groups are attached is

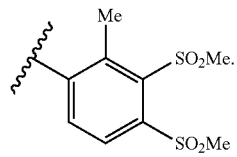 [SMILES: *c1ccc(S(C)(=O)=O)c(S(C)(=O)=O)c1C]

In another specific embodiment, the phenyl ring to which the $R^{18}$ groups are attached is

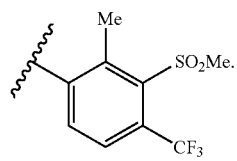

In yet another specific embodiment, the phenyl ring to which the $R^{18}$ groups are attached is

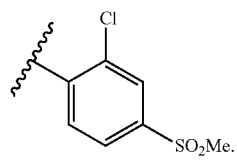 [SMILES: *c1ccc(S(C)(=O)=O)cc1Cl]

In an embodiment, L is —$NR^{19}$—$CH_2$—. Preferably, $R^{19}$ is H. Thus, L may be —$NHCH_2$—. Alternatively, L may be —O—N═CH—. In another alternative, L may be —N═CH—. In yet another alternative embodiment, L is —$NR^{19}SO_2$—. Thus, L may be $NHSO_2$.

In an embodiment, $Z^1$ is $CR^{17}$, e.g. CH. Alternatively, $Z^1$ is N.

In an embodiment, $Z^2$ is $CR^{17}$, e.g. CH. Preferably, $Z^2$ is N.

In an embodiment, $R^{21}$ is H. In another embodiment, $R^{21}$ is $C_1$-$C_4$ alkyl, e.g. methyl.

In an embodiment, Z is $CR^{17}$, e.g. CH. Preferably, Z is N. In a preferred embodiment, the heterocyclic portion of compounds of formulae XX, XXV and XXVI is

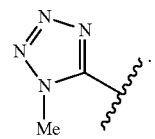

In an embodiment, $Z^1$ is $CR^{17}$, e.g. CH. Alternatively, $Z^1$ is N.

In an embodiment, $Z^2$ is $CR^{17}$, e.g. CH. Alternatively, $Z^2$ is N.

In an embodiment $R^{22}$ is

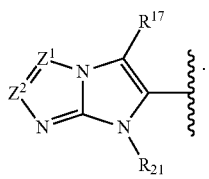

In another embodiment, $R^{22}$ is

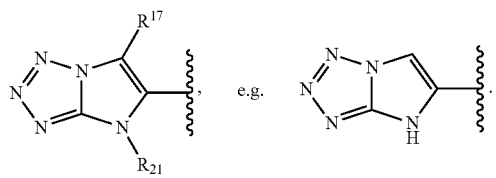, e.g.

In yet another embodiment, $R^{22}$ is

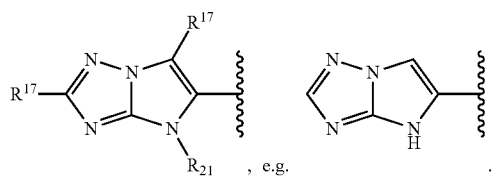, e.g.

In an embodiment, $R^{22}$ is

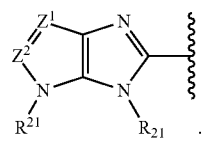

In another embodiment, $R^{22}$ is

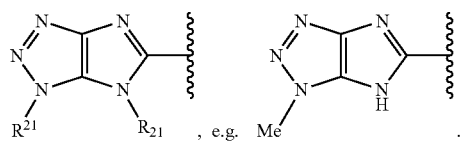, e.g. Me

In any of the above aspects and embodiments, heteroaryl groups may be any aromatic (i.e. a ring system containing $2(2n+1)\pi$ electrons) 5-10 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine, indole, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine, naphthyridine. Heteroaryl groups may also be 6-membered heteroaryl groups in which the heteroaromatic ring is substituted with 1 heteroatomic group independently selected from O, S and NH and the ring also comprises a carbonyl group. Such groups include pyridones and pyranones.

In any of the above aspects and embodiments, a heterocycloalkyl group is a 3-8 membered saturated or partially ring comprising 1 or 2 heteroatoms independently selected from O, S and N (in other words from 1 to 2 of the atoms forming the ring system are selected from O, S and N). By partially saturated it is meant that the ring may comprise one or two double bonds. This applies particularly to rings with from 5 to 8 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine.

In any of the above aspects and embodiments, a haloalkyl group may have any amount of halogen substituents. The group may contain a single halogen substituent, it may have two or three halogen substituents, or it may be saturated with halogen substituents.

In an embodiment, in any $R^1$-$R^{22}$ group which contains an aryl or heteroaryl group, that aryl or heteroaryl group is optionally substituted, where chemically possible, by 1 to 4 substituents which are each independently selected at each occurrence from the group consisting of: $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$; and $OR^a$; wherein $R^a$ is selected from H, $C_1$-$C_4$ alkyl and $C_1$-$C_4$ haloalkyl; and wherein any two substituents on neighbouring atoms and comprising $R^a$ groups may join up to form a ring.

In an embodiment, in any $R^1$-$R^{22}$ group which contains an alkyl, haloalkyl, cycloalkyl, or heterocycloalkyl group, that alkyl, haloalkyl, cycloalkyl or heterocycloalkyl group is optionally substituted, where chemically possible, by 1 to 4 substituents which are each independently selected at each occurrence from the group consisting of: oxo; $=NR^a$; $=NOR^2$; $R^2$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$; and $OR^a$; wherein $R^a$ is selected from H, $C_1$-$C_4$ alkyl and $C_1$-$C_4$ haloalkyl.

A group which is represented as $SO_3R$ is typically a group having the form $S(O)_2OR$. A group which is represented as $S(O)_2R$ is typically a group having the form $S(O)_2R$. A group which is represented as $SO_2NR^aR^a$ is typically a group having the form $S(O)_2NRR$.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

The compounds of the invention may be obtained, stored and/or used in the form of an agronomically acceptable salt. Suitable salts include, but are not limited to, salts of acceptable inorganic acids such as hydrochloric, sulphuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae I to XXIX and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Isotopically-labelled compounds can generally be prepared by conventional techniques known to those skilled in the art or by processes analogous to those described using an appropriate isotopically-labelled reagent in place of the non-labelled reagent previously employed.

Throughout this specification these abbreviations have the following meanings:
DCE—dichloromethane
DCM—dichloromethane
DMAP—N,N-dimethyl-4-aminopyridine
DMF—dimethylformamide
DMSO—dimethylsulfoxide
mCPBA—meta-chloroperbenzoic acid
THF—tetrahydrofuran
TLC—thin layer chromatography
TMS—trimethylsilyl Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as herbicides.

According to another aspect of the present invention, there is provided a method for controlling the weeds, the method comprising applying an agronomically effective and substantially non-phytotoxic (to the crop plant) quantity of a compound according to the invention to the plants themselves or to the area where it is intended that the plants will grow.

The pesticide may be applied as a foliar application, stem application, drench or drip application (chemigation) to the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a herbicidal composition comprising an effective amount of an active compound of the invention. The composition may further comprise one or more additional herbicides.

The term "effective and non-phytotoxic amount" means an amount of pesticide according to the invention which is sufficient to control or destroy any of the targeted pests present or liable to appear in the crops and which does not have any significant detrimental effect on the crops or indeed has a positive effect on plant vigour and yield in the absence of target organism. The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known herbicides for example, to improve the activity spectrum or to reduce or slow the development of resistance.

A mixture with other known active compounds such as nematicides, acaricides, fungicides, insecticides or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating the soil: from 0.1 to 10 000 g/ha, preferably from 1 to 5000 g/ha.

A formulation which could be used to administer the compounds, particularly in the context of testing for activity, would be to supply all compounds as a 10% solution in DMSO. If there are solubility problems this can be helped by adding acetone (e.g. to dilute a DMSO solution/suspension by 50% resulting in a 5% solution of the compound in DMSO/acetone. The administration formulation is then obtained by adding the DMSO (or DMSO/acetone) solution to a 0.1% solution of Tween 20™ in water to give the required concentration. The result is likely to be an emulsion that can be sprayed. If crystallisation occurs, resulting in inconsistent results, further DMSO can be added to the test solution.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples pears peaches nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular nematodes, which are encountered in agriculture, in horticulture, in animal husbandry, in forests, in gardens and leisure facilities, in the protection of stored products and of materials, and in the hygiene sector. They may be preferably employed as crop protection agents.

Use as Herbicides

Some compounds of the invention may also have herbicidal activity against a broad spectrum of economically important mono- and dicotyledonous harmful plants. Some compounds of the invention may have herbicidal activity against monocotyledonous plants but no activity or little activity against dicotyledonous crops. Other compounds of the invention may be selective, having excellent herbicidal activity against dicotyledonous plants but no activity or little activity against monocotyledonous crops.

Difficult-to-control perennial weeds which produce shoots from rhizomes, root stocks or other perennial organs may also be controlled by herbicidal compounds. Here, the substances can be applied by the pre-sowing method, the pre-emergence method and/or the post-emergence method.

The following are illustrative examples of monocotyledonous weeds that may be controlled by herbicidal compounds: *Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and also *Bromus* spp. such as *Bromus catharticus*, *Bromus secalinus*, *Bromus erectus*, *Bromus tectorum* and *Bromus japonicus* and *Cyperus* species from the annual group, and, *Agropyron*, *Cynodon*, *Imperata* and *Sorghum* and also perennial *Cyperus* species, from the perrenial group.

The following are illustrative examples of dicotyledonous weeds that may be controlled by herbicidal compounds: *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., in the case of annuals, and *Convolvulus*, *Cirsium*, *Rumex* and *Artemisia* in the case of the perennials.

If herbicidal compounds are applied to the soil surface before or during germination, the weed seedlings are inhibited or prevented completely from emerging or else the weeds grow until they have reached the cotyledon stage, but then their growth stops, and, eventually, they die completely.

If herbicidal compounds are applied post-emergence to the green parts of the plants, growth typically stops following the treatment, and the weed plants remain substantially at the growth stage of the point of time of application, or they die completely, so that in this manner competition from the weeds is eliminated quickly and in a sustained manner.

DETAILED DESCRIPTION—SYNTHESIS

The skilled man will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions); "March's Advanced Organic Chemistry—Reactions, Mechanisms and Structure", M B Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Certain compounds of the invention can be made according to the following general synthetic schemes. Certain compounds of the invention can be made according to or analogously to the methods described in Examples 1 to 4.

General Synthetic Schemes

Scheme A

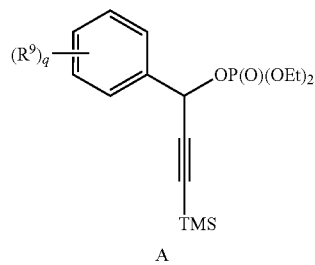

A

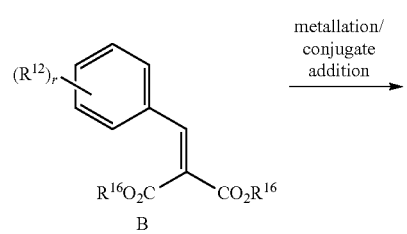

B

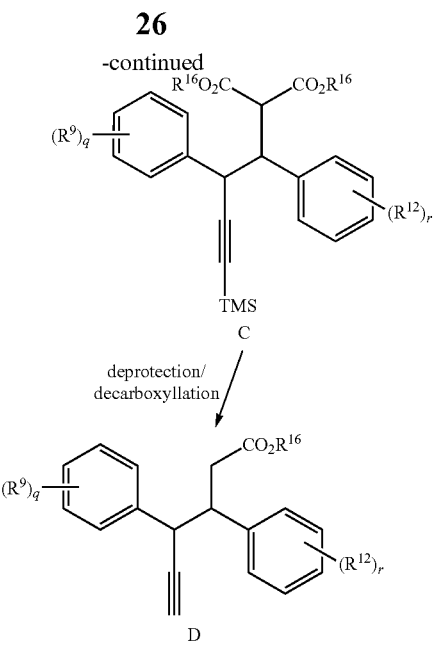

A metallation reaction (e.g. using $(^{i}PrO)_4Ti$ and $^{i}PrMgCl$ optionally in ether at room temperature) on alkyne A followed by conjugate addition to alkene B can provide compound C. Removal of the TMS protecting group (e.g. using $K_2CO_3$ optionally in methanol at room temperature) followed by decarboxylation (for compounds in which $R^{16}$ is Me or Et this reaction can be conducted in the presence of LiCl in DMSO at 150° C.) can provide alkyne D. Compounds in which $R^{16}$ is H can typically be made according to this route using a methyl or ethyl ester and then hydrolysing that ester (e.g. using NaOH and water optionally in THF at room temperature) to generate the carboxylic acid. This route is particularly useful for compounds of formula IX, examples of which are compounds 1 and 2:

Scheme B

1

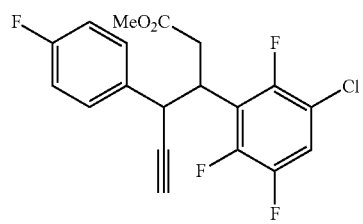

2

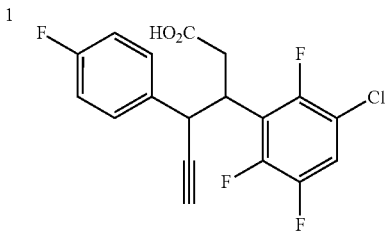

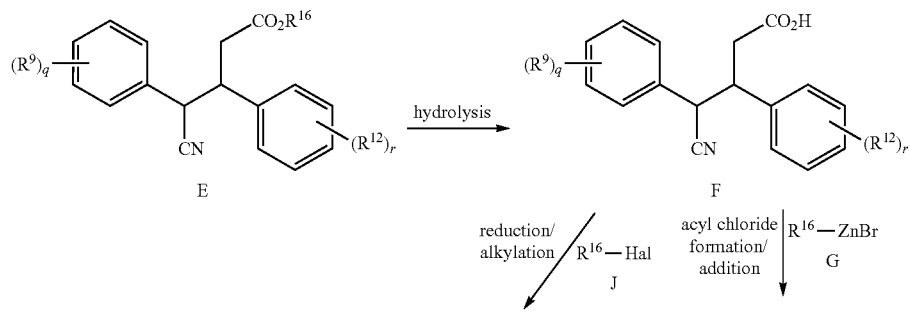

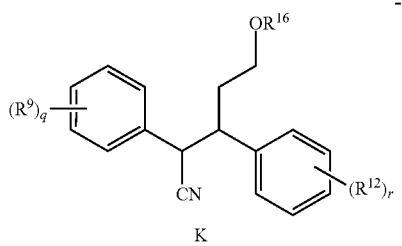

K

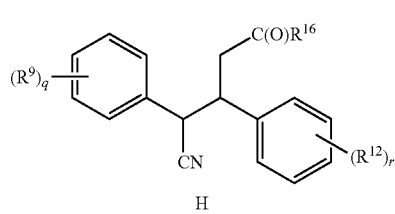

H

Compounds of formula E can be synthesised as described in WO2011/098417. Ester hydrolysis (e.g. using NaOH and water optionally in THF at room temperature) can generate the carboxylic acid F. Acid F can be converted to the acid chloride (e.g. using $SOCl_2$) which can undergo reaction with organozinc agent G to form the ketone H. Alternatively, acid F can be converted to a mixed anhydride (e.g. using $ClCO_2Me$ and triethylamine optionally in THF at room temperature) which upon reduction (e.g. using $NaBH_4$ in ethanol optionally at room temperature) can provide an alcohol which can be alkylated using alkylating agent J (e.g. using $NaNH_2$ optionally in $Et_2O$ at room temperature) to provide ether K. This route is particularly useful for compounds of formulae X and XI, examples of which are compounds 3 and 4:

-continued

O

An aldol like reaction (e.g. using $CeCl_3$ optionally in THF at room temperature, followed by BuLi optionally in $Et_2O$ and THF at room temperature with an acidic work up) between nitrile L and aldehyde M can, once the product has been acylated with acyl chloride N (e.g. using DMAP and triethylamine optionally in DCM at room temperature), provide compounds of formula O. This route is particularly useful for compounds of formula XIV, an example of which is compound 5:

Scheme C

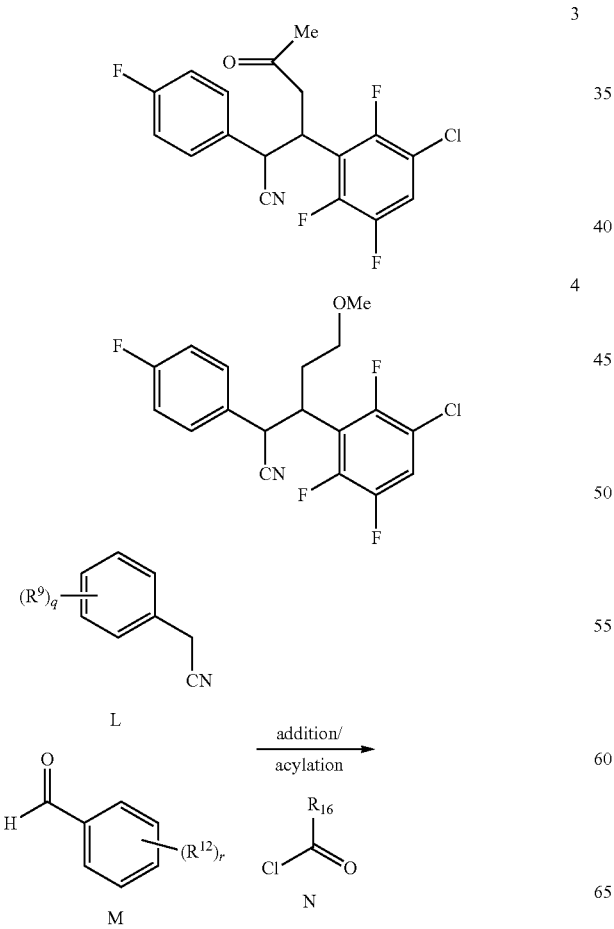

Scheme D

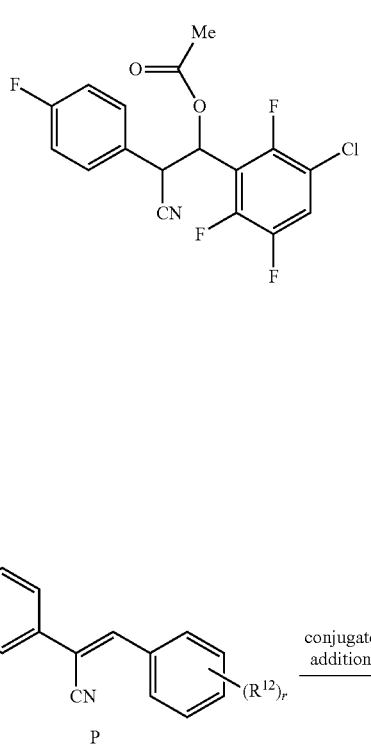

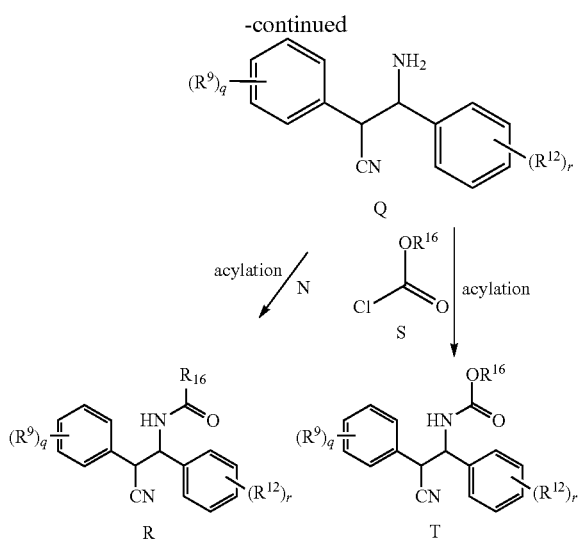

An alternative set of reaction conditions (e.g. NaOMe optionally in ethanol at room temperature) can be used to convert L and M to condensation product P. Addition of ammonia (e.g. in isopropanol at room temperature) can provide amine Q. Subsequent acylation with acyl chloride N or chloroformate S (e.g. using DMAP and triethylamine optionally in DCM at room temperature), can provide compounds of formula R or T respectively. This route is particularly useful for compounds of formulae XII and XIII, examples of which are compounds 6 and 7:

Nitrile L can also react with epoxide U (e.g. through initial deprotonation with BuLi optionally in THF at −78° C. followed by $NH_4Cl$ work up) to generate an alcohol which, upon mesylation (e.g. with $MeSO_2Cl$ and $NEt_3$ optionally in DCM at 0° C.), can provide mesylate W. Displacement of the mesylate with tBuSH (e.g. in the presence of $Cs_2CO_3$ optionally in MeCN at reflux) can, following oxidation (e.g. using mCPBA optionally in DCM and water at room temperature), provide compounds of formula Y in which $R^{16}$ is H. Alternatively, displacement with $Na_2SO_3$ (optionally in water at room temperature) can provide compounds of formula Z. In yet another alternative, displacement with a phosphite (i.e. $P(OR^{16})_3$ with the reaction optionally conducted in the presence of $Bu_4NI$ at 150° C.) can provide compounds of formula AA. For compounds of formula AA in which $R^{16}$ is H the compounds may preferably be made by reacting W with a trialkylphosphite (e.g. $P(OMe)_3$) and subsequently hydrolysing the phosphate ester groups (e.g. using TMSBr and $TMSCH_2CH=CH_2$ at room temperature followed by $NH_4HCO_3$). This route is particularly useful for compounds of formulae XV, XVI and XVII, examples of which are compounds 8, 9 and 10:

Scheme E

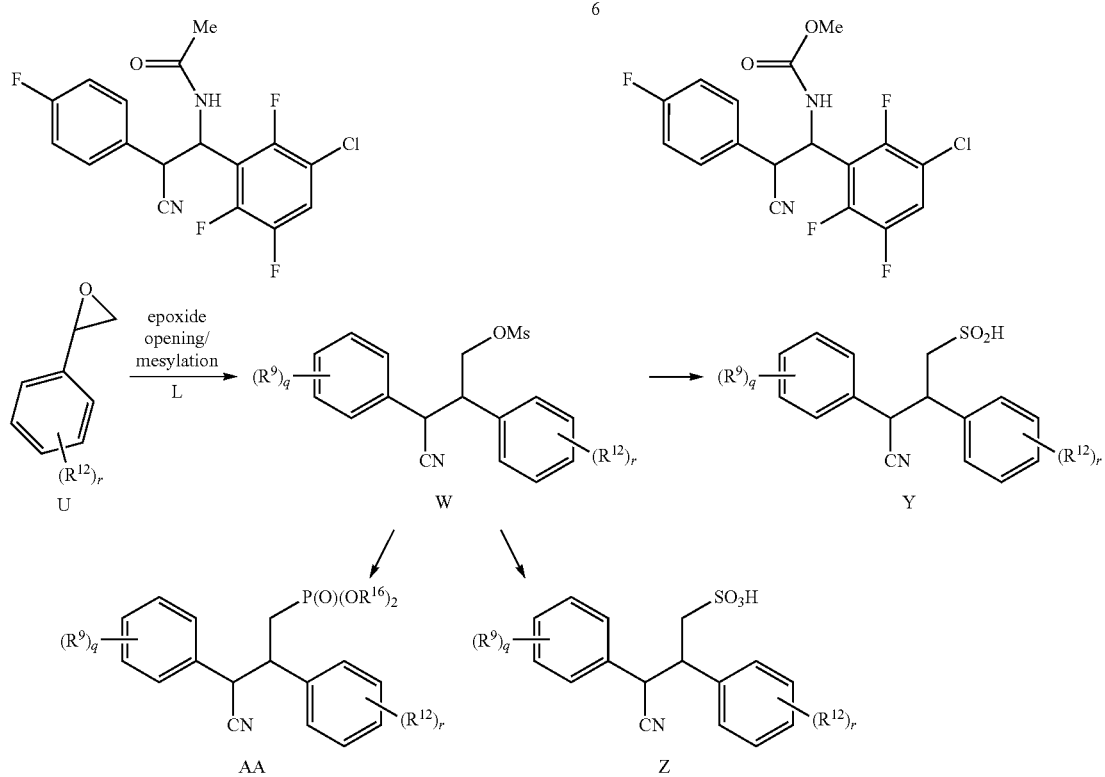

Scheme F

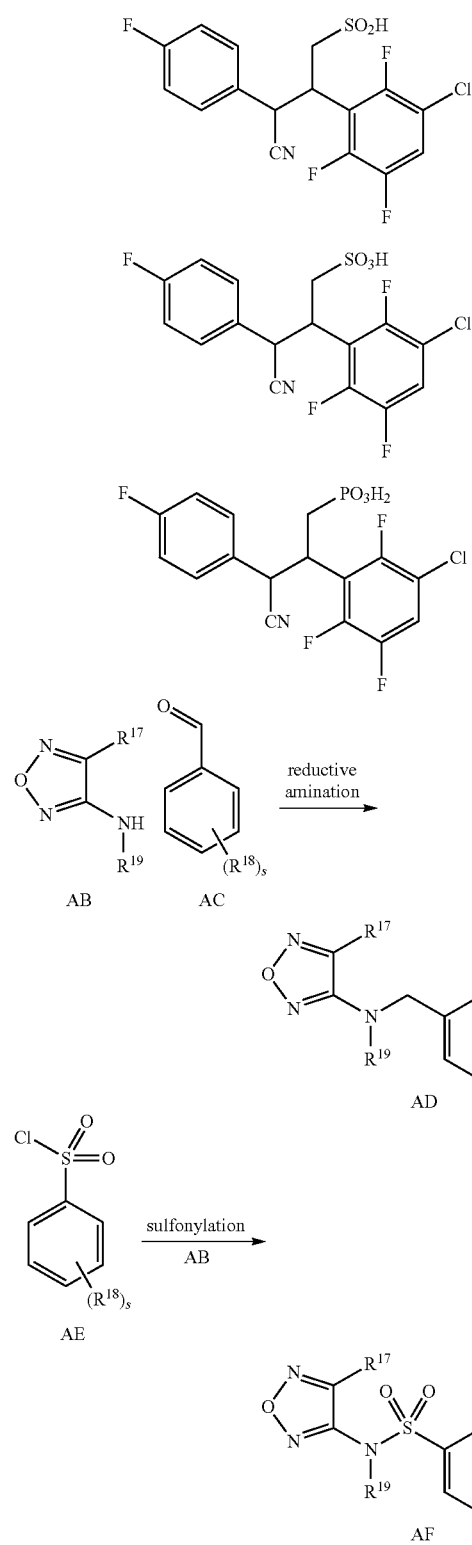

Scheme G

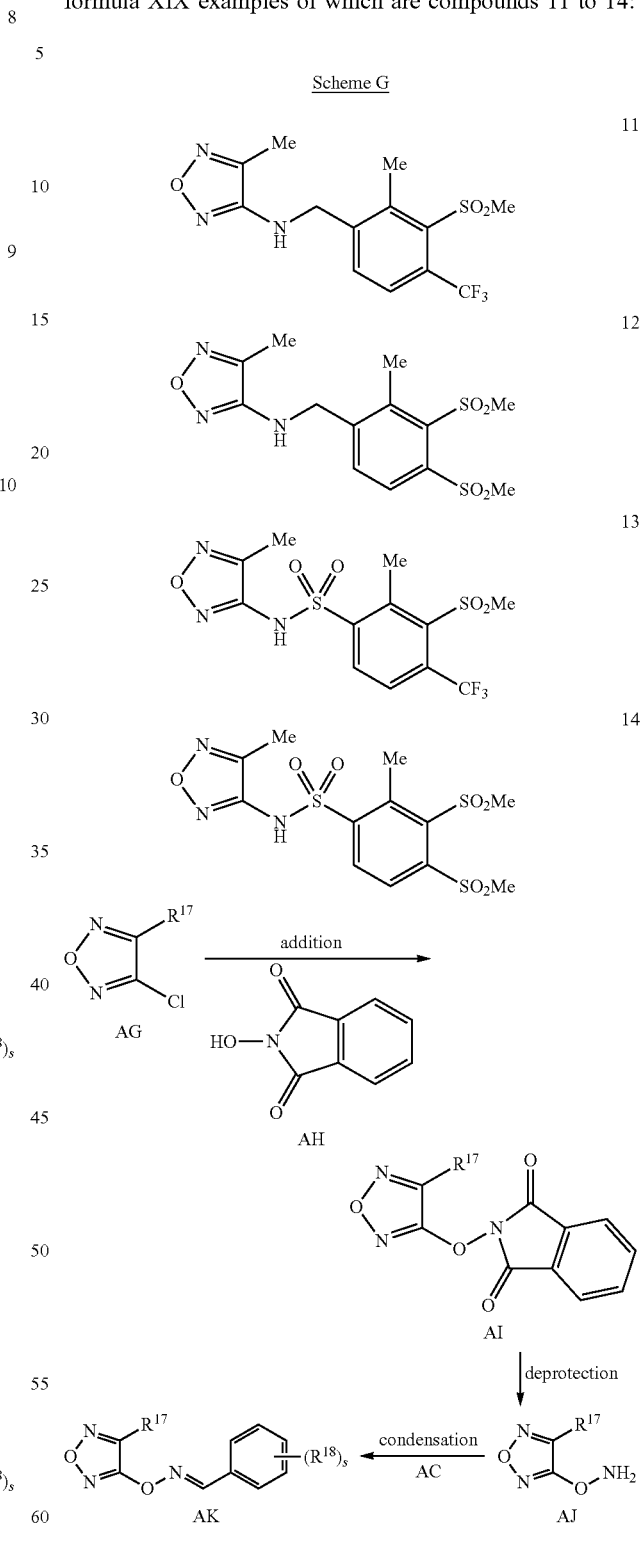

dine optionally at room temperature) can provide sulphonamide AF. This route is particularly useful for compounds of formula XIX examples of which are compounds 11 to 14:

A reductive amination reaction between amine AB and aldehyde AC (e.g. using NaBH$_3$CN optionally in methanol at room temperature) can provide amine AD. Reaction between amine AB and sulfonyl chloride AE (e.g. in pyri- Treatment of chloride AG with compound AH (e.g. using NaH optionally in THF at room temperature) can provide AI. Subsequent deprotection (e.g. with N$_2$H$_4$ optionally in ethanol at room temperature) can provide hydroxylamine AJ. Condensation between aldehyde AC and hydroxylamine AJ can provide oxime AK. This route is particularly useful for compounds of formula XIX, examples of which are compounds 15 and 16:

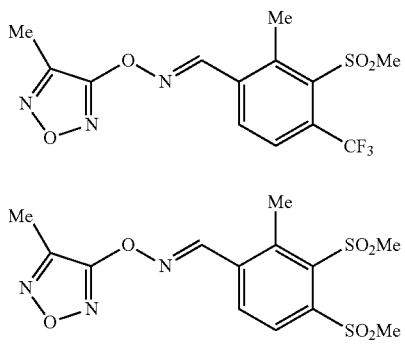

The route described in Scheme G can also be used, with the appropriate starting chloride to prepare the compounds of formula XX, an example of which is compound 17:

Scheme H

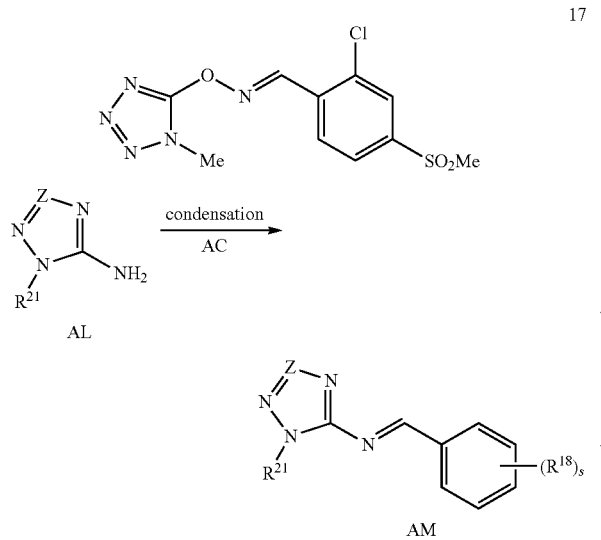

A condensation reaction (e.g. in ethanol at 80° C.) between amine AL and aldehyde AC can provide imine AM. This route is particularly useful for compounds of formula XX, an example of which is compound 18:

Scheme I

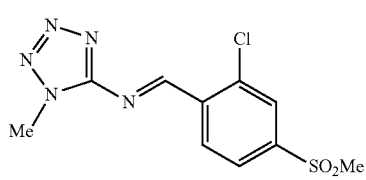

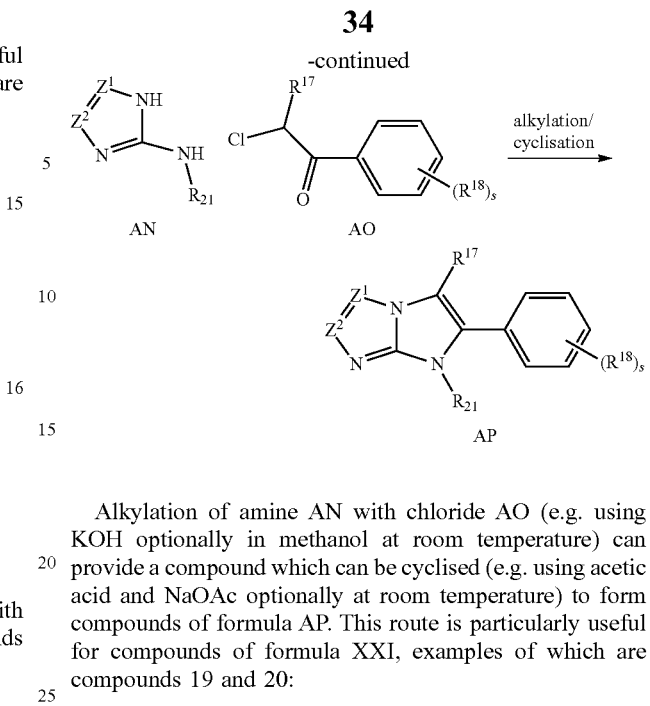

Alkylation of amine AN with chloride AO (e.g. using KOH optionally in methanol at room temperature) can provide a compound which can be cyclised (e.g. using acetic acid and NaOAc optionally at room temperature) to form compounds of formula AP. This route is particularly useful for compounds of formula XXI, examples of which are compounds 19 and 20:

Scheme J

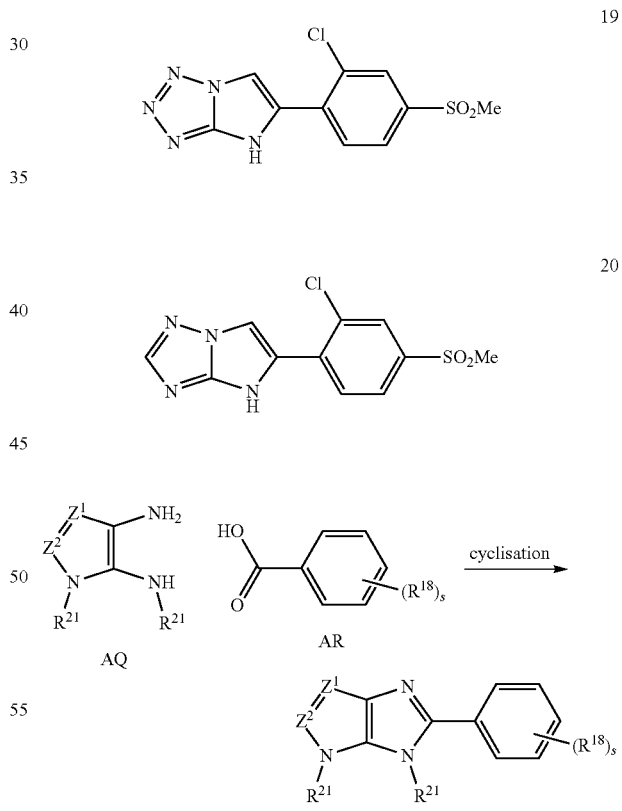

A condensation/cyclisation (e.g. using $POCl_3$ optionally at 100° C.) between diamine AQ and carboxylic acid AR can provide fused imidazole AS. This route is particularly useful for compounds of formula XXI, an example of which is compound 21:

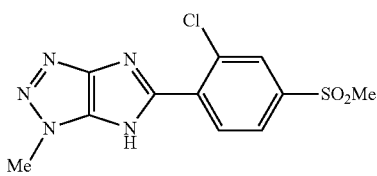

EXAMPLES

Flash chromatography was carried out using silica gel (40-63 μm particles). Thin layer chromatography was carried out on pre-coated aluminium backed plates (Merck silica Keiselgel 60 $F_{254}$). Visualisation was carried out with UV light (254 nm) and by staining with either potassium permanganate, phosphomolybdic acid (PMA) or ninhydrin solutions. Where hexane is specified as a flash chromatography solvent, petroleum ether (b.p. 40-60° C.) can be used as an alternative.

All $^1$H NMR spectra were obtained using either a Bruker Ultrashield 300 spectrometer or Bruker DPX300 spectrometer. Chemical shifts are expressed in parts per million (δ) and are referenced to the solvent. Coupling constants J are expressed in Hertz (Hz).

ESI mass spectrometry was performed using a Bruker HCT Ultra LCMS instrument (Agilent 1200 Series LC with diode array detector and Bruker HCT Ultra Ion Trap MS) using a Phenomenex Luna 5u C18(2) 100 Å, 50×2.00 mm 5 micron LC column (solvent: 5-90% gradient of acetonitrile in water (with 1% formic acid). Flow rate 1.2 mL/min). EI mass spectrometry was performed using a Varian Saturn 2100T GC/MS instrument with a FactorFour VF-5MS 30 m×0.25 mm capillary column. High resolution mass spectrometry (ESI) was performed using a Dionex UltiMate 3000 system.

All reagents were obtained from commercial suppliers and used as supplied unless otherwise stated.

Example 1

1-[4-Chloro-2-fluoro-5-[(E)-(isopropyl(methyl)sulfamoyl)iminomethyl]phenyl]-3-methyl-2,6-dioxo-4-(trifluoromethyl)pyrimidine 22

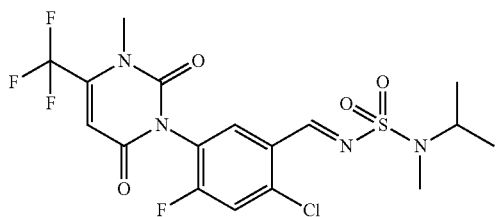

2-[Methyl(sulfamoyl)amino]propane (217 mg, 1.43 mmol) was added to a suspension of 2-chloro-4-fluoro-5-[3-methyl-2,6-dioxo-4-(trifluoromethyl)pyrimidin-1-yl] benzaldehyde (WO 97/30060; EP 542685; 500 mg, 1.43 mmol) in toluene (5 mL) under nitrogen in the presence of QuadraPure™ SA and molecular sieves. The reaction mixture was heated at reflux for 20 hours before addition of a further portion of 2-[methyl(sulfamoyl)amino]propane (40 mg, 0.26 mmol). The heating was continued for a further 4 hours, after which time TLC showed complete consumption of the starting aldehyde. The reaction mixture was filtered through celite and the resulting filtrate was dried in vacuo. The crude material was purified by flash chromatography on silica gel (solvent 75:25 hexane/EtOAc) to afford the product as a colourless oil (124 mg, 18%).

NMR $δ_H$ (CDCl$_3$, 300 MHz): 9.17 (s, 1H), 8.03 (d, J=7.5 Hz, 1H), 7.35 (d, J=9.0 Hz, 1H), 6.31 (s, 1H), 4.23-4.14 (m, 1H), 3.50 (s, 3H), 2.68 (s, 3H), 1.09 (d, J=7.5 Hz, 6H). ESI-MS 485.0 [MH]$^+$.

1-[4-Chloro-2-fluoro-5-[[(isopropyl(methyl)sulfamoyl)amino]methyl]phenyl]-3-methyl-2,6-dioxo-4-(trifluoromethyl)pyrimidine 23

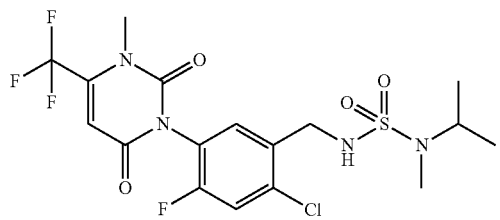

2-[Methyl(sulfamoyl)amino]propane (211 mg, 1.39 mmol) was added to a suspension of 2-chloro-4-fluoro-5-[3-methyl-2,6-dioxo-4-(trifluoromethyl)pyrimidin-1-yl] benzaldehyde (486 mg, 1.39 mmol) in toluene (5 mL) under nitrogen in the presence of molecular sieves. The reaction mixture was heated at reflux for 21 hours, after which time TLC showed complete consumption of the starting aldehyde. The reaction mixture was filtered through celite and the resulting filtrate was dried in vacuo to afford the imine product as a brown residue (640 mg). Sodium (triacetoxy) borohydride (1.47 g, 6.95 mmol) was added to a portion of the imine (500 mg) in DCE (5 mL) under nitrogen in the presence of molecular sieves. The reaction mixture was stirred at ambient temperature for 18 hours, after which time TLC showed complete consumption of the imine. 2 M HCl$_{(aq)}$ (20 mL) was added and the reaction mixture was extracted with DCM (3×25 mL) and then the organics were washed with brine (3×25 mL) before being dried over MgSO$_4$ and the solvent removed in vacuo. The crude material was purified by flash chromatography on silica gel (solvent 65:35 hexane/EtOAc) to afford the product as a yellow solid (194 mg).

NMR $δ_H$ (CDCl$_3$, 300 MHz): 7.37 (d, J=7.5 Hz, 1H), 7.23 (d, J=9.0 Hz, 1H), 6.23 (s, 1H), 4.76 (t, J=6.5 Hz, 1H), 4.17 (d, J=6.5 Hz, 2H), 4.02 (sept, J=6.5 Hz, 1H), 3.50 (s, 3H), 2.57 (s, 3H), 1.06 (d, J=6.5 Hz, 6H). ESI-MS 487.1 [MH]$^+$.

N-[[2-Chloro-4-fluoro-5-[3-methyl-2,6-dioxo-4-(trifluoromethyl)pyrimidin-1-yl]phenyl]methyl]-3-methyl-butane-2-sulfonamide 24

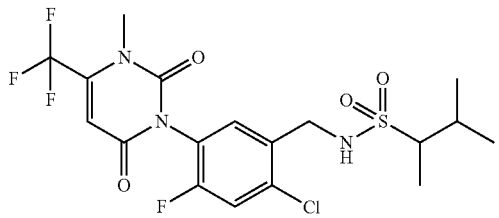

To ammonium hydroxide solution (28% NH$_3$ in H$_2$O, 75 mL) was added a solution of 3-methyl-2-butanesulfonyl chloride (3.90 g, 22.9 mmol) in chloroform (75 mL) dropwise and the mixture was stirred at room temperature for 1 h. The reaction mixture was diluted with tetrahydrofuran (25 mL) and extracted with chloroform (2×50 mL). The combined organic extracts were washed with brine (2×50 mL) and 2 M hydrochloric acid (5 mL), dried over MgSO$_4$ and the solvent removed in vacuo. The oil was purified by flash chromatography on silica gel (solvent 40% EtOAc/hexane) to afford 3-methylbutane-2-sulfonamide as a brown oil (0.68 g, 20%). $^1$H NMR $\delta_H$ (CDCl$_3$, 300 MHz): 4.50 (br, 2H), 2.94 (dq, J=7.1, 3.0 Hz, 1H), 2.43 (spt d, J=6.9, 2.8 Hz, 1H), 1.29 (d, J=7.0 Hz, 3H), 0.97 (m, 6H).

3-Methylbutane-2-sulfonamide (84 mg, 0.55 mmol) was added to a suspension of 2-chloro-4-fluoro-5-[3-methyl-2,6-dioxo-4-(trifluoromethyl)pyrimidin-1-yl]benzaldehyde (175 mg, 0.50 mmol) in toluene (2 mL) under nitrogen in the presence of molecular sieves. The reaction mixture was heated at reflux for 72 hours, after which time reaction mixture was filtered through celite and the resulting filtrate was dried in vacuo to afford the imine product as a brown residue (200 mg). Sodium (triacetoxy)borohydride (106 g, 0.50 mmol) was added to the imine in DCE (2 mL) under nitrogen in the presence of molecular sieves. The reaction mixture was stirred at ambient temperature for 72 hours, after which time TLC showed complete consumption of the imine. 2 M HCl$_{(aq)}$ (10 mL) was added and the reaction mixture was extracted with EtOAc (3×20 mL) and then the organics were washed with brine (3×25 mL) before being dried over MgSO$_4$ and the solvent removed in vacuo. The crude material was purified by flash chromatography on silica gel (solvent 65:35 hexane/EtOAc) to afford the product as a yellow oil (137 mg, 56%).

NMR $\delta_H$ (CDCl$_3$, 300 MHz): 7.38 (dd, J=2.5, 7.5 Hz, 1H), 7.26 (d, J=9.0 Hz, 1H), 6.24 (s, 1H), 4.75-4.66 (m, 1H), 4.32 (d, J=6.5 Hz, 1H), 3.45 (s, 3H), 2.77-2.69 (m, 1H), 2.35-2.28 (m, 1H), 1.23-1.15 (m, 3H), 0.95-0.85 (m, 6H). ESI-MS 486.1 [MH]$^+$.

2-Chloro-4-fluoro-N-(isopropyl(methyl)sulfamoyl)-5-[3-methyl-2,6-dioxo-4-(trifluoromethyl)pyrimidin-1-yl]benzamide 25

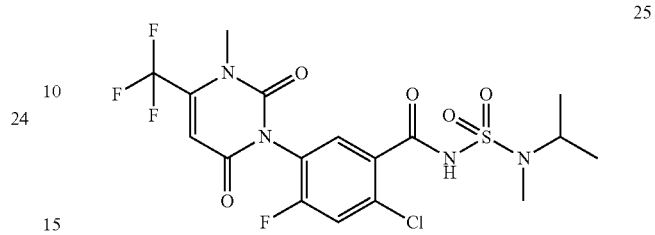

2-chloro-4-fluoro-5-[3-methyl-2,6-dioxo-4-(trifluoromethyl)pyrimidin-1-yl]benzoic acid was prepared according to the procedure provided in US 2004/0018942. 2-[Methyl(sulfamoyl)amino]propane was prepared according to the procedure provided in US 2010/0216774. A solution of 2-chloro-4-fluoro-5-[3-methyl-2,6-dioxo-4-(trifluoromethyl)pyrimidin-1-yl]benzoic acid (732 mg, 2 mmol) and carbonyldiimidazole (486 mg, 3 mmol) in THF (10 mL) was heated at reflux for 1 hour under nitrogen. After cooling to ambient temperature, 2-[methyl(sulfamoyl)amino]propane (456 mg, 3 mmol) was added followed by 1,8-diazabicyclo[5.4.0]undec-7-ene (0.45 mL, 3 mmol) and the reaction mixture was stirred at ambient temperature for 24 hours, after which time TLC showed complete consumption of the starting material. The reaction mixture was diluted with water (40 mL) and 2 M HCl$_{(aq)}$ (10 mL) and extracted with EtOAc (3×25 mL) and then the organics were washed with brine (2×50 mL) before being dried over MgSO$_4$ and the solvent removed in vacuo. The crude material was purified by flash chromatography on silica gel (solvent 60:40 hexane/EtOAc) to afford the title compound as a white solid (470 mg, 47%).

NMR $\delta_H$ (CDCl$_3$, 300 MHz): 9.12 (br, 1H), 7.71 (d, J=9.0 Hz, 1H), 7.40 (d, J=9.0 Hz, 1H), 6.39 (s, 1H), 4.35-4.26 (m, 1H), 3.58 (s, 3H), 2.97 (s, 3H), 1.22 (d, J=6.0 Hz, 6H). ESI-MS 501.0 [MH]$^+$.

Compound 25 (saflufenacil) forms part of the prior art.

2-Chloro-N-(1,2-dimethylpropylsulfonyl)-4-fluoro-5-[3-methyl-2,6-dioxo-4-(trifluoromethyl)pyrimidin-1-yl]benzamide 26

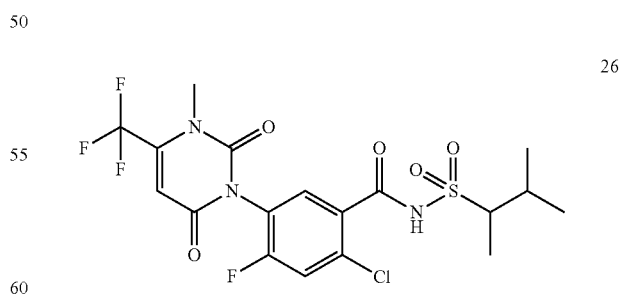

Oxalyl chloride (85 μL, 1.0 mmol) was added to a solution of 2-chloro-4-fluoro-5-[3-methyl-2,6-dioxo-4-(trifluoromethyl)pyrimidin-1-yl]benzoic acid (188 mg, 0.5 mmol) in DCM (2 mL) and DMF (1 drop) under nitrogen. After 1 hour, the volatiles were removed in vacuo and DMAP (88 mg, 0.7 mmol), N,N-diisopropylethylamine (0.87 mL, 5.0 mmol) and toluene (1 mL) were added. A solution of 3-methylbutane-2-sulfonamide (302 mg, 2.0 mmol) in toluene (2 mL) was added and the reaction was heated at reflux under nitrogen for 20 hours, after which time TLC showed complete consumption of the starting material. The reaction mixture was quenched with water (15 mL) and 2 M HCl$_{(aq)}$ (10 mL) and extracted with EtOAc (3×25 mL) and then the organics were washed with brine (2×25 mL) before being dried over MgSO$_4$ and the solvent removed in vacuo. The crude material was purified by flash chromatography on silica gel (solvent 60% hexane/EtOAc) to afford the title compound as an off-white solid (152 mg, 61% as a 1:1 mixture of diastereoisomers).

NMR $\delta_H$ (CDCl$_3$, 300 MHz): NMR $\delta_H$ (CDCl$_3$, 300 MHz): 9.30 (s, 0.5H), 9.27 (s, 0.5H), 7.65 (d, 7.5 Hz, 0.5H), 7.64 (d, 7.5 Hz, 0.5H), 7.38 (s, 0.5H), 7.35 (s, 0.5H), 6.23 (s, 1H), 3.77 (dq, J=7.1, 2.9 Hz, 1H), 3.62 (s, 3H), 2.59 (spt d, J=6.9, 2.8 Hz, 1H), 1.38 (d, J=7.0 Hz, 3H), 1.08 (d, J=6.9 Hz, 3H), 1.05 (d, J=6.6 HZ, 3H).

ESI-MS 500.1 [MH]$^+$.

Example 2

Ethyl 4-cyano-3-(2,6-difluorophenyl)-4-(4-fluorophenyl)butanoate 27

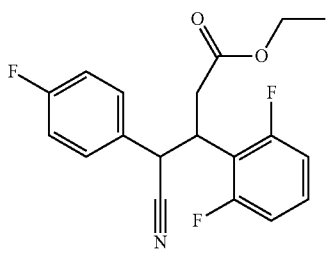 [SMILES: CCOC(=O)CC(c1c(F)cccc1F)C(C#N)c1ccc(F)cc1]

Ethyl (E)-3-(2,6-difluorophenyl)prop-2-enoate was prepared according to the procedure provided in WO 2011126567. A solution of 4-fluorophenylacetonitrile (1.27 g, 1.13 mL, 9.43 mmol) was added dropwise over 5 minutes to a stirred suspension of potassium tert-butoxide (1.06 g, 9.43 mmol) in tetrahydrofuran (40 mL) at −78° C. The mixture was stirred at −78° C. for 10 minutes and a solution of ethyl (E)-3-(2,6-difluorophenyl)prop-2-enoate (2.00 g, 9.43 mmol) in tetrahydrofuran (4 mL) was added dropwise over 5 minutes to the mixture. The mixture was stirred at −78° C. for 1 hour before 2M aqueous hydrochloric acid (50 mL) and EtOAc (200 mL) were added to the mixture. The separated organic phase was washed with saturated aqueous sodium hydrogen carbonate (50 mL) and brine (50 mL), dried over MgSO$_4$ and concentrated in vacuo. The residue was purified by flash chromatography on silica gel (solvent hexane moving to 25% EtOAc/hexane) to afford the title compound as a colourless oil (3.05 g, 93% containing a 2:1 mixture of diastereoisomers).

$^1$H NMR (300 MHz, CDCl$_3$): 7.42-7.23 (m, 2H), 7.21-7.04 (m, 2.33H), 6.96-6.90 (m, 2H), 6.75 (t, J=8.4 Hz, 0.67H), 4.28 (d, J=9.9 Hz, 0.67H), 4.21-3.92 (m, 3H), 4.15 (s, 0.33H), 3.24-3.11 (m, 0.67H), 2.83 (dd, J=16.5 and 9.0 Hz, 0.67H), 2.67 (dd, J=16.2 and 6.0 Hz, 0.67H), 1.15 (t, J=7.2 Hz, 1H), 1.12 (t, J=7.2 Hz, 2H).

ESI-MS 370.0 [M+Na$^+$].

Compound 27 forms part of the prior art (WO2013/010882) and is included for reference only.

4-Cyano-3-(2,6-difluorophenyl)-4-(4-fluorophenyl)butanoic acid 27a

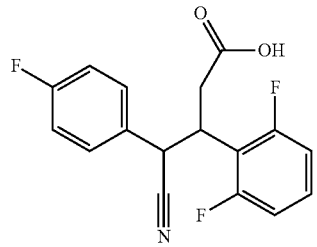 [SMILES: N#CC(c1ccc(F)cc1)C(CC(=O)O)c1c(F)cccc1F]

A solution of ethyl 4-cyano-3-(2,6-difluorophenyl)-4-(4-fluorophenyl)butanoate 27 (800 mg, 2.30 mmol) and lithium hydroxide (61 mg, 2.53 mmol) in tetrahydrofuran (10 mL) and water (1 mL) was stirred at 45° C. for 6 hours. A further portion of lithium hydroxide (41 mg, 1.73 mmol) was added to the mixture, and the mixture was then heated to 45° C. for 3 hours. After cooling to rt, water (50 mL) and dichloromethane (20 mL) were added to the mixture and the separated aqueous phase was washed with dichloromethane (3×20 mL). The pH of the aqueous phase was adjusted to pH 1 by dropwise addition of 2M aqueous hydrochloric acid and was extracted with dichloromethane (3×40 mL). The combined organic fractions were then dried over MgSO$_4$ and concentrated in vacuo to afford the title compound as a colourless oil which solidified on standing (656 mg, 89% containing a 1:1 ratio of diastereoisomers).

$^1$H NMR (300 MHz, CDCl$_3$): 7.39-7.23 (m, 2H), 7.21-7.02 (m, 2H), 6.93 (apr t, J=8.7 Hz, 2H), 6.73 (t, J=8.7 Hz, 1H), 4.24 (d, J=9.9 Hz, 0.5H), 4.19-4.01 (m, 1H), 4.13 (s, 0.5H), 3.25 (dd, J=17.1 and 4.5 Hz, 0.5H), 3.15 (dd, J=16.8 and 9.0 Hz, 0.5H), 2.88 (dd, J=17.1 and 8.4 Hz, 0.5H), 2.73 (dd, J=16.8 and 6.0 Hz, 0.5H); ESI-MS 342.0 [M+Na$^+$].

3-(2,6-Difluorophenyl)-2-(4-fluorophenyl)-5-hydroxy-pentanenitrile 28

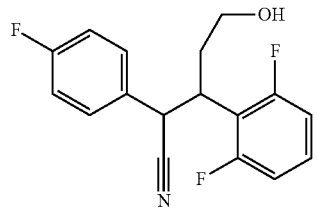 [SMILES: N#CC(c1ccc(F)cc1)C(CCO)c1c(F)cccc1F]

A solution of borane tetrahydrofuran complex (2.35 mL, 2.35 mmol, 1.0M in tetrahydrofuran) was added dropwise over 15 minutes to a stirred solution of 4-cyano-3-(2,6-difluorophenyl)-4-(4-fluorophenyl)butanoic acid 27 (500 mg, 1.57 mmol) in tetrahydrofuran (15 ml) and the mixture was stirred at room temperature for 16 h. Methanol (10 mL) was carefully added dropwise over 15 minutes to the mixture and the mixture was concentrated in vacuo. The residue was re-dissolved in methanol (10 mL) and concentrated in vacuo with this process repeated three times. The residue was dissolved in a 1:1 mixture of EtOAc/petrol (50 mL) and the organic phase was filtered through celite and silica, eluting with a 1:1 mixture of EtOAc/petrol (100 mL) before the filtrate was concentrated in vacuo. The residue was dissolved in EtOAc (100 mL) and the organic phase was washed with water (25 mL), saturated aqueous sodium hydrogen carbonate (25 mL) and brine (25 mL), dried over MgSO$_4$ and concentrated in vacuo to afford the title compound as a colourless oil (478 mg, 100% containing a 1:1 mixture of diastereoisomers).

$^1$H NMR (300 MHz, CDCl$_3$): 7.43-7.23 (m, 1H), 7.20-7.04 (m, 3H), 7.01-6.83 (m, 2H), 6.74 (apr t, J=8.7 Hz, 1H), 4.17 (d, J=9.0 Hz, 0.5H), 4.12 (d, J=11.4 Hz, 0.5H), 3.83-3.57 (m, 1H), 3.50-3.20 (m, 1H), 2.50-2.37 (m, 0.5H), 2.26-2.10 (m, 0.5H), 1.96-1.85 (m, 0.5H), 1.75-1.65 (m, 0.5H), 1.50 (br. s, 0.5H), 1.34 (br. s, 0.5H).

ESI-MS 306.0 [M+H$^+$].

3-(2,6-Difluorophenyl)-2-(4-fluorophenyl)-5-hydroxy-2-methyl-pentanenitrile 29

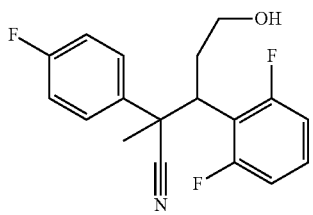 [SMILES: CC(C#N)(c1ccc(F)cc1)C(CCO)c1c(F)cccc1F]

A solution of 3-(2,6-difluorophenyl)-2-(4-fluorophenyl)-5-hydroxy-pentanenitrile 28 (350 mg, 1.15 mmol) in tetrahydrofuran (2 mL) was added dropwise over 5 minutes to a stirred suspension of sodium hydride (55 mg, 1.38 mmol, 60% dispersed in mineral oil) in tetrahydrofuran (10 mL) at 0° C. The mixture was stirred at 0° C. for 10 minutes before iodomethane (244 mg, 0.11 mL, 1.72 mmol) was added dropwise over 2 minutes to the mixture. The mixture was warmed to room temperature and stirred for 16 h before water (50 mL) and EtOAc (50 mL) were added to the mixture. The separated aqueous phase was extracted with EtOAc (2×50 mL) and the combined organic fractions were dried MgSO$_4$ and concentrated in vacuo. The residue was purified by flash chromatography on silica gel (solvent 10% EtOAc/hexane moving to 40% EtOAc/hexane) to afford the title compound as a colourless oil (124 mg, 34% containing a single diastereoisomer).

$^1$H NMR (300 MHz, CDCl$_3$): 7.39-7.25 (m, 2H), 7.22-7.08 (m, 1H), 7.01-6.88 (m, 2H), 6.80-6.71 (m, 2H), 3.82 (dd, J=12.3 and 3.9 Hz, 1H), 3.74-3.62 (m, 1H), 3.33 (td, J=10.2 and 4.9 Hz, 1H), 2.50-2.33 (m, 1H), 2.28-2.12 (m, 1H), 1.93 (s, 3H), 1.57 (br. s, 1H).

ESI-MS 342.0 [M+Na$^+$].

4-Cyano-3-(2,6-difluorophenyl)-4-(4-fluorophenyl) pentanoic acid 30

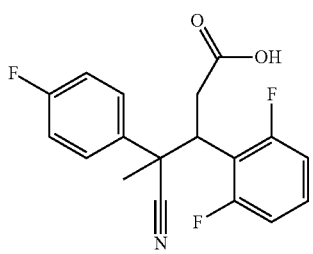 [SMILES: CC(C#N)(c1ccc(F)cc1)C(CC(=O)O)c1c(F)cccc1F]

A solution of 3-(2,6-difluorophenyl)-2-(4-fluorophenyl)-5-hydroxy-2-methyl-pentanenitrile 29 (75 mg, 0.24 mmol) in chloroform (0.75 mL) and acetonitrile (0.75 mL) was added dropwise over 5 minutes to a stirred solution of sodium periodate (206 mg, 1.00 mmol) in water (1 mL) at room temperature. Ruthenium(III) chloride (5 mg, 0.03 mmol) was added in 1 portion to the mixture and the mixture was then stirred at room temperature for 16 h. Water (10 mL) and EtOAc (10 mL) were added to the mixture and the separated aqueous phase was extracted with EtOAc (3×10 mL) before the combined organic fractions were dried over MgSO$_4$ and concentrated in vacuo. The residue was purified by flash chromatography on silica gel (solvent 6% EtOAc/hexane) to afford the title compound as a colourless solid (55 mg, 71% containing a single diastereoisomer).

$^1$H NMR (300 MHz, CDCl$_3$): 7.38-7.25 (m, 2H), 7.24-7.12 (m, 1H), 6.98 (t, J=9.0 Hz, 2H), 6.84-6.69 (m, 2H), 4.09 (dd, J=10.2 and 4.8 Hz, 1H), 3.21 (dd, J=16.8 and 10.2 Hz, 1H), 2.99 (dd, J=17.1 and 4.8 Hz, 1H), 1.88 (s, 3H).

ESI-MS 356.2 [M+Na$^+$].

2-Bromo-2-(2,6-difluorophenyl)ethanol 31

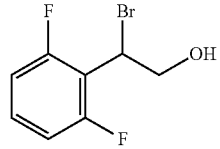 [SMILES: OCC(Br)c1c(F)cccc1F]

2-(2,6-Difluorophenyl)oxirane was prepared according to the procedure provided in Dou et al. Bioorganic & Medicinal Chemistry (2010), 18(3), 1093-1102. A biphasic solution of 2,6-difluorophenyl)oxirane (2.29 g, 14.7 mmol) in hydrobromic acid (5 mL, 48% in water) and chloroform (40 mL) was vigorously stirred at room temperature for 30 minutes. Water (100 mL) and dichloromethane (100 mL) were added to the mixture. The separated aqueous phase was extracted with dichloromethane (100 mL) and the combined organic fractions were then washed with saturated aqueous sodium hydrogen carbonate (50 mL), dried over MgSO$_4$ and concentrated in vacuo to afford the title compound as a light yellow oil (3.48 g, 100%).

$^1$H NMR (300 MHz, CDCl$_3$): 7.40-7.25 (m, 1H), 6.95 (apr t, J=8.4 Hz, 2H), 5.43 (ddt, J=9.9, 6.0 and 1.5 Hz, 1H), 4.42-4.29 (m, 1H), 4.17-4.01 (m, 1H), 2.16 (br. t, J=5.0 Hz, 1H).

[2-Bromo-2-(2,6-difluorophenyl)ethoxy]-tert-butyl-dimethyl-silane 32

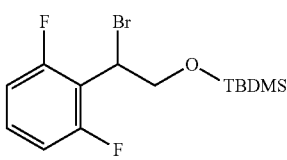

tert-Butyldimethylsilyl chloride (2.37 g, 15.7 mmol) was added in one portion to a stirred solution of 2-bromo-2-(2,6-difluorophenyl)ethanol 31 (3.73 g, 15.7 mmol) and imidazole (1.28 g, 18.9 mmol) in N,N-dimethylformamide (4 mL) and the mixture was stirred at room temperature for 1 hour. Water (100 mL) and petrol (100 mL) were added to the mixture. The separated aqueous phase was extracted with petrol (100 mL) and the combined organic fractions were then dried over MgSO₄ and concentrated in vacuo to afford the title compound as a light yellow oil (4.071 g, 74%).

¹H NMR (300 MHz, CDCl₃): 7.34-7.20 (m, 1H), 6.90 (apr t, J=8.4 Hz, 2H), 5.32-5.26 (m, 1H), 4.27-4.13 (m, 2H), 0.80 (s, 9H), 0.06 (s, 3H), −0.02 (s, 3H).

4-(tert-Butyl(dimethyl)silyl)oxy-3-(2,6-difluorophenyl)-2-(4-fluorophenyl)butanenitrile 33

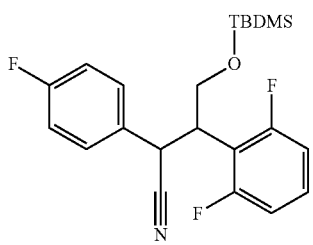

Potassium tert-butoxide (1.95 g, 17.4 mmol) was added in one portion to a stirred solution of 4-fluorophenylacetonitrile (2.35 g, 2.09 mL, 17.4 mmol) and [2-bromo-2-(2,6-difluorophenyl)ethoxy]-tert-butyl-dimethyl-silane 32 (4.07 g, 11.6 mmol) in tetrahydrofuran (50 mL) and the mixture was heated to 50° C. for 5 hours. Water (250 mL) and petrol (150 mL) were added to the mixture. The separated aqueous phase was extracted with petrol (150 mL) and the combined organic fractions were then dried over MgSO₄ and concentrated in vacuo. The residue was purified by flash chromatography on silica gel (solvent hexane moving to 4% EtOAc/hexane) to afford the title compound as a light yellow oil (4.92 g, 78% containing a 3:2 mixture of diastereoisomers).

¹H NMR (300 MHz, CDCl₃): 7.39-7.29 (m, 1H), 7.25-7.16 (m, 1H), 7.16-7.03 (m, 2H), 6.97-6.84 (m, 2H), 6.73 (t, J=9.0 Hz, 1H), 4.62 (d, J=9.0 Hz, 0.4H), 4.27-4.06 (m, 0.8H), 4.14 (d, J=6.0 Hz, 0.6H), 3.97-3.62 (m, 1.2H), 0.82 (s, 3.6H), 0.81 (s, 5.4H), 0.02 (s, 1.8H), −0.05 (s, 1.8H), −0.08 (s, 1.2H), −0.10 (s, 1.2H).

ESI-MS 406.2 [M+H⁺].

3-(2,6-Difluorophenyl)-2-(4-fluorophenyl)-4-hydroxy-butanenitrile 34

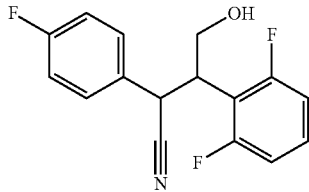 [SMILES: N#CC(c1ccc(F)cc1)C(CO)c1c(F)cccc1F]

A solution of hydrogen fluoride pyridine (1.07 mL, 7.39 mmol, ~70% hydrogen fluoride) was added dropwise over 10 minutes to a stirred solution of 4-(tert-butyl(dimethyl) silyl)oxy-3-(2,6-difluorophenyl)-2-(4-fluorophenyl)butanenitrile 33 (2.50 g, 6.16 mmol) in tetrahydrofuran (40 mL) at room temperature in a plastic container. The mixture was stirred at room temperature for 16 h before saturated aqueous sodium hydrogen carbonate (200 mL) was carefully added dropwise over 1 hour to the mixture followed by EtOAc (100 mL). The separated aqueous phase was extracted with EtOAc (100 mL) and the combined organic fractions were washed with water (50 mL), 0.5M aqueous hydrochloric acid (50 mL), saturated aqueous sodium hydrogen carbonate (50 mL) and brine (50 mL) before being dried over MgSO₄ and concentrated in vacuo. The residue was purified by flash chromatography on silica gel (solvent hexane moving to 30% EtOAc/hexane) to afford the title compound as a colourless oil (1.70 g, 95% containing a 3:2 mixture of diastereoisomers).

¹H NMR (300 MHz, CDCl₃): 7.42-7.24 (m, 1H), 7.23-7.05 (m, 2.8H), 7.01-6.88 (m, 2H), 6.78 (t, J=8.7 Hz, 1.2H), 4.54 (d, J=9.6 Hz, 0.4H), 4.41-4.08 (m, 1.4H), 4.28 (d, J=11.1 Hz, 0.6H), 3.98-3.71 (m, 1.6H), 1.76 (t, J=6.0 Hz, 0.6H), 1.57 (t, J=6.0 Hz, 0.4H).

ESI-MS 292.0 [M+H⁻].

3-(2,6-difluorophenyl)-2-(4-fluorophenyl)-3-hydroxy-propanenitrile 35

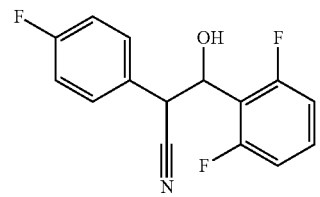 [SMILES: N#CC(c1ccc(F)cc1)C(O)c1c(F)cccc1F]

A solution of 4-fluorophenylacetonitrile (1.35 g, 10.0 mmol) was added dropwise over 5 minutes to a stirred suspension of potassium tert-butoxide (1.12 g, 10.0 mmol) in tetrahydrofuran (20 mL) at −78° C. The mixture was stirred at −78° C. for 10 minutes before a solution of 2,6-difluorobenzaldehyde (1.42 g, 10.0 mmol) in tetrahydrofuran (2 mL) was added dropwise over 5 minutes to the mixture. The mixture was stirred at −78° C. for 1 hour before 2M aqueous hydrochloric acid (50 mL) and EtOAc (200 mL) were added to the mixture. The separated organic phase was washed with saturated aqueous sodium hydrogen carbonate (50 mL) and brine (50 mL), dried over MgSO₄ and concentrated in vacuo. The residue was purified by flash chromatography on silica gel (solvent 10% EtOAc/hexane) to afford the title compound as a colourless oil which solidified on standing (2.25 g, 81% containing a 3:2 mixture of diastereoisomers).

¹H NMR (300 MHz, CDCl₃): 7.42-7.28 (m, 1H), 7.27-7.06 (m, 2.8H), 6.95 (apr t, J=8.4 Hz, 2H), 6.83 (apr t, J=8.4 Hz, 1.2H), 5.35-5.32 (m, 1H), 4.37 (d, J=8.4 Hz, 0.4H), 4.36 (d, J=9.0 Hz, 0.6H), 3.05 (br. s, 0.6H), 2.64 (br. s, 0.4H).

ESI-MS 300.0 [M+Na⁺].

Ethyl 3-(2,6-difluorophenyl)-4-(4-fluorophenyl)-6-trimethylsilyl-hex-5-ynoate 36

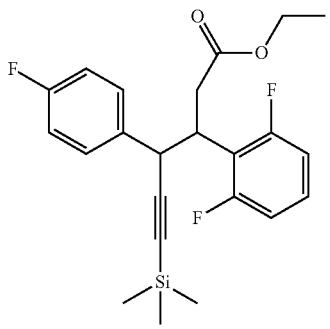 [SMILES: CCOC(=O)CC(c1c(F)cccc1F)C(C#C[Si](C)(C)C)c1ccc(F)cc1]

3-(4-Fluorophenyl)prop-1-ynyl-trimethyl-silane was prepared according to the process provided in WO 2011/034832. A solution of 3-(4-fluorophenyl)prop-1-ynyl-trimethyl-silane (615 mg, 3.0 mmol) in THF (4 mL) was cooled to −78° C. and treated with potassium tert-butoxide (335 mg, 3.0 mmol) in one portion. The mixture was stirred for 10 minutes before a solution of ethyl (E)-3-(2,6-difluorophenyl)prop-2-enoate (633 mg, 3.0 mmol) in THF (4 mL) was added dropwise. The mixture was stirred for 1 h before 2N HCl (4 mL) and EtOAc (4 mL) were added and the mixture allowed to come to RT over 16 h. The organic layer was separated, the aqueous layer was extracted with EtOAc (2×10 mL), the combined organics dried over MgSO$_4$ and the solvent removed in vacuo. The residue was purified by flash chromatography on silica gel (solvent hexane moving to 5% EtOAc/hexane) to afford the title compound contaminated with ethyl 3-(2,6-difluorophenyl)-4-(4-fluorophenyl)hex-5-ynoate (620 mg) The material was taken forward into future reactions without further purification.

Ethyl 3-(2,6-difluorophenyl)-4-(4-fluorophenyl)hex-5-ynoate 37

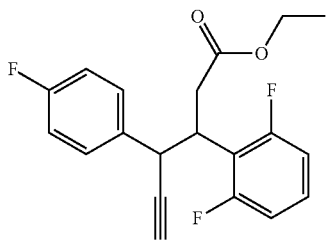 [SMILES: C#CC(c1ccc(F)cc1)C(CC(=O)OCC)c1c(F)cccc1F]

A solution of ethyl 3-(2,6-difluorophenyl)-4-(4-fluorophenyl)-6-trimethylsilyl-hex-5-ynoate 36 (500 mg, 1.20 mmol) and potassium carbonate (165 mg, 1.20 mmol) in ethanol (10 mL) was stirred at room temperature overnight. The mixture was concentrated in vacuo and the residue was dissolved in EtOAc (25 ml) and water (25 mL). The separated organic phase was dried over MgSO$_4$ and concentrated in vacuo. The residue was purified by flash chromatography on silica gel (solvent 3% EtOAc/hexane) to afford the title compound as a colourless solid (260 mg, 63% containing a 2:1 mixture of diastereoisomers).

$^1$H NMR (300 MHz, CDCl$_3$): 7.42-7.31 (m, 0.67H), 7.26-6.98 (m, 3H), 6.94-6.78 (m, 2H), 6.69 (apr t, J=8.7 Hz, 1.33H), 4.08-3.83 (m, 4H), 3.33 (dd, J=16.2 and 4.2 Hz, 0.67H), 3.03 (m, 0.67H), 2.78 (dd, J=15.9 and 9.6 Hz, 0.33H), 2.53 (dd, J=15.9 and 5.4 Hz, 0.33H), 2.40 (d, J=2.1 Hz, 0.67H), 2.10 (d, J=2.1 Hz, 0.33H), 1.11 (t, J=7.2 Hz, 2H), 1.07 (t, J=7.2 Hz, 1H).
EI-MS 346.2 [M$^+$].

Methyl 3-(2,6-difluorophenyl)-4-(4-fluorophenyl)hex-5-ynoate 38

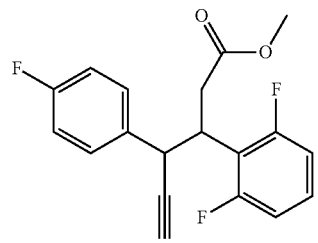 [SMILES: C#CC(c1ccc(F)cc1)C(CC(=O)OC)c1c(F)cccc1F]

A solution of ethyl 3-(2,6-difluorophenyl)-4-(4-fluorophenyl)-6-trimethylsilyl-hex-5-ynoate 36 (100 mg, 0.24 mmol) and potassium carbonate (33 mg, 0.24 mmol) in methanol (2 mL) was stirred at room temperature for 4 hours. The mixture was concentrated in vacuo and the residue was purified by flash chromatography on silica gel (solvent 3% EtOAc/hexane) to afford the title compound as a colourless solid (30 mg, 40% containing a 5:3 mixture of diastereoisomers).

$^1$H NMR (300 MHz, CDCl$_3$): 7.42-7.31 (m, 0.75H), 7.26-6.98 (m, 3H), 6.94-6.78 (m, 2H), 6.71 (t, J=8.4 Hz, 1.25H), 4.11-3.88 (m, 2H), 3.59 (s, 1.88H), 3.49 (s, 1.12H), 3.35 (dd, J=15.6 and 3.6 Hz, 0.63H), 3.06 (dd, J=15.6 and 9.6 Hz, 0.63H), 2.81 (dd, J=15.9 and 9.0 Hz, 0.37H), 2.60 (dd, J=15.9 and 5.1 Hz, 0.37H), 2.40 (d, J=2.1 Hz, 0.63H), 2.11 (d, J=2.4 Hz, 0.37H). EI-MS 332.2 [M$^+$].

3-(2,6-difluorophenyl)-4-(4-fluorophenyl)hex-5-ynoic acid 39

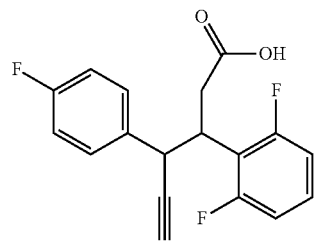 [SMILES: C#CC(c1ccc(F)cc1)C(CC(=O)O)c1c(F)cccc1F]

A solution of ethyl 3-(2,6-difluorophenyl)-4-(4-fluorophenyl)hex-5-ynoate 37 (160 mg, 0.48 mmol) and lithium hydroxide (13 mg, 0.53 mmol) in tetrahydrofuran (3 mL) and water (0.3 mL) was stirred at 45° C. for 8 hours. A further portion of lithium hydroxide (13 mg, 0.53 mmol) was added to the mixture and the mixture was then heated to 45° C. for 40 hours. Water (20 mL) and dichloromethane (10 mL) were added to the mixture and the separated aqueous phase was washed with dichloromethane (3×10 mL). The pH of the aqueous phase was adjusted to pH 1 by dropwise addition of 2M aqueous hydrochloric acid and was extracted with dichloromethane (3×15 mL) before the combined organic fractions were dried over MgSO4 and concentrated in vacuo to afford the title compound as a colourless oil which solidified on standing (125 mg, 82% containing a 2:1 ratio of diastereoisomers).

¹H NMR (300 MHz, CDCl₃): 7.40-7.29 (m, 0.67H), 7.26-6.95 (m, 3H), 6.95-6.75 (m, 2H), 6.69 (t, J=8.7 Hz, 1.33H), 4.06-3.81 (m, 2H), 3.36 (dd, J=16.8 and 3.9 Hz, 0.67H), 3.07 (dd, J=16.8 and 10.5 Hz, 0.67H), 2.82 (dd, J=16.8 and 9.3 Hz, 0.33H), 2.62 (dd, J=16.8 and 5.4 Hz, 0.33H), 2.38 (d, J=2.1 Hz, 0.67H), 2.11 (d, J=2.4 Hz, 0.33H).

ESI-MS 319.1 [M+H]⁺.

Example 3

2-Bromo-1-(2-chloro-4-(methylsulfonyl)phenyl) ethanone 41

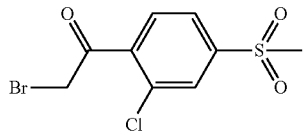

1-(2-Chloro-4(methylsulfonyl)phenyl)ethanone was prepared according to the procedure provided in Zuo et al. Shijie Nongyao (2007), 29(6), 15-21. A solution of bromine (0.2 mL, 3.92 mmol) in chloroform (5 mL) was added dropwise to a suspension of 1-(2-chloro-4(methylsulfonyl) phenyl)ethanone (960 mg, 4.13 mmol) and aluminium chloride (10 mg, 0.08 mmol) in chloroform (10 mL) at −5° C. The mixture was warmed to ambient temperature and stirred for 20 hours, after which time the reaction was quenched by addition of water (5 mL). The aqueous layer was extracted with chloroform (3×15 mL) before the combined organics were washed with brine (20 mL), dried over MgSO4 and the solvent removed in vacuo. The crude material was purified by flash chromatography on silica gel (solvent 50% EtOAc/hexane) to afford the title compound as a white solid (1.03 g, 80%).

¹H NMR δ_H (CDCl₃, 300 MHz): 8.08 (s, 1H), 7.97 (d, J=6.0 Hz, 1H), 7.74 (d, J=6.0 Hz, 1H), 4.49 (s, 2H), 3.13 (s, 3H) ppm. ESI-MS 312.9 [MH]⁺.

5-(2-Chloro-4-methylsulfonylphenyl)-3H-imidazol[2,1][1,2,4]triazole 42

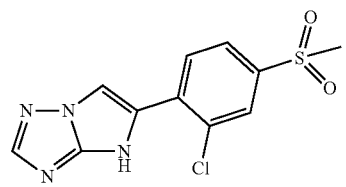 [SMILES: CS(=O)(=O)c1ccc(-c2cn3ncnc3[nH]2)c(Cl)c1]

3-Amino-1,2,4-triazole (311 mg, 3.71 mmol) was dissolved in toluene (5 mL) and heated to 110° C. A solution of 2-bromo-1-(2-chloro-4-(methylsulfonyl)phenyl ethanone 41 (550 mg, 1.85 mmol) in toluene (10 mL) (with the minimum amount of DMF needed for full dissolution) was added portion wise to the solution over 3 hours. The reaction was maintained at this temperature for 16 hours after which time TLC showed complete consumption of the starting material. The volatiles were removed in vacuo before the crude material was purified by flash chromatography on silica gel (solvent EtOAc) to afford the title compound as a yellow solid (90 mg, 8%).

¹H NMR δ_H (DMSO-d6, 300 MHz): 8.51 (s, 1H), 8.31 (d, J=9.0 Hz, 1H), 8.05 (s, 1H), 7.93 (s, 1H), 7.84 (d, J=9.0 Hz, 1H), 3.21 (s, 3H) ppm. ESI-MS 297.0 [MH]⁺.

5-(2-Chloro-4-methylsulfonylphenyl)-1-methyl-6H-pyrazolo[3,4-d]imidazole 43

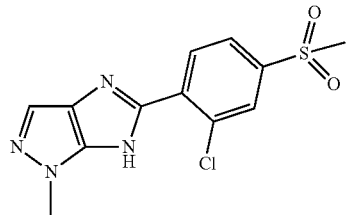 [SMILES: Cn1ncc2nc(-c3ccc(S(C)(=O)=O)cc3Cl)[nH]c21]

Phosphorus(V) oxychloride (21.18 mL, 22.72 mmol) was added to a mixture of 1-methyl-1H-4,5-diamine (844 mg, 5.68 mmol) and 2-chloro-4-(methylsulfonyl)benzoic acid (1.33 g, 5.68 mmol) and the mixture heated at 100° C. for 20 hours after which time TLC showed complete consumption of the starting material. The reaction was allowed to cool before being poured onto ice (~100 g). DCM (50 mL) was added before the mixture was made alkaline using 50% NaOH_(aq). A precipitate formed which was removed by filtration. The organic layer was separated and the aqueous layer was extracted with DCM (2×50 mL) before the organics were combined, washed with brine (2×50 mL), dried over MgSO4 and the solvent removed in vacuo. The crude material was purified by flash chromatography on silica gel (solvent 2% MeOH/EtOAc) to afford the title compound as a yellow solid (193 mg, 11%).

¹H NMR δ_H (DMSO-d6, 300 MHz): 12.49 (br, 1H), 8.15-8.02 (m, 2H), 8.02-7.99 (m, 1H), 7.45 (s, 1H), 3.91 (s, 3H). (1 signal (3H) is missing beneath the residual solvent peak). ESI-MS 311.0 [MH]⁺.

Example 4

2-Methyl-3-methylsulfanyl-4-(trifluoromethyl)benzaldehyde 45

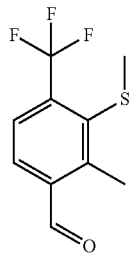

2-Methyl-3-methylsulfanyl-4-(trifluoromethyl)benzoic acid was prepared according to the procedure provided in WO 2008125214. Borane-THF complex (2.6 mL, 1M in tetrahydrofuran, 2.60 mmol) was added to a solution of 2-methyl-3-methylsulfanyl-4-(trifluoromethyl)benzoic acid (260 mg, 1.04 mmol) in tetrahydrofuran (3 mL) and the mixture was stirred at room temperature for 17 h. Methanol (1 mL) was added, followed by water (10 mL) and ethyl acetate (15 mL) and the mixture was extracted with ethyl acetate (2×15 mL). The combined organic phases were dried over MgSO$_4$ and the solvent removed in vacuo. Dess-Martin periodinane (453 mg, 1.07 mmol) was added to a solution of this crude product (240 mg, 1.02 mmol) in dichloromethane (8 mL) and the mixture was stirred at room temperature for 1.5 h. Saturated aqueous sodium bicarbonate solution (10 mL) was added and the mixture was extracted with dichloromethane (3×15 mL). The combined organic phases were dried over MgSO$_4$ and concentrated to give the crude product which was purified by flash chromatography on silica gel (solvent 10% EtOAc/hexane) to afford the title compound as a colourless oil (192 mg, 81%).

$^1$H NMR $\delta_H$ (300 MHz, CDCl$_3$); 10.34 (s, 1H), 7.81 (d, J=8.0 Hz, 1H), 7.69 (d, J=8.0 Hz, 1H), 2.94 (s, 3H), 2.22 (s, 3H); EI-MS 234.0 [M$^+$].

1-[2-Methyl-3-methylsulfanyl-4-(trifluoromethyl)phenyl]-N-(4-methyl-1,2,5-oxadiazol-3-yl)methanimine 46

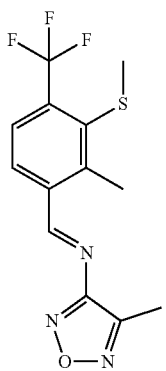

A solution of 2-methyl-3-methylsulfanyl-4-(trifluoromethyl)benzaldehyde 45 (184 mg, 0.788 mmol) and 4-methyl-1,2,5-oxadiazol-3-amine (78 mg, 0.788 mmol) in toluene (3 mL) was heated at 110° C. over 4 Å molecular sieves and MgSO$_4$ for 96 h after which time the mixture was filtered and concentrated to give the title compound as a colourless solid (176 mg, 71%).

$^1$H NMR $\delta_H$ (300 MHz, CDCl$_3$); 9.31 (s, 1H), 8.16 (d, J=8.0 Hz, 1H), 7.63 (d, J=8.0 Hz, 1H), 2.88 (s, 3H), 2.37 (s, 3H), 2.22 (s, 3H); EI-MS 315 [M$^+$].

4-Methyl-N-[[2-methyl-3-methylsulfanyl-4-(trifluoromethyl)phenyl]methyl]-1,2,5-oxadiazol-3-amine 47

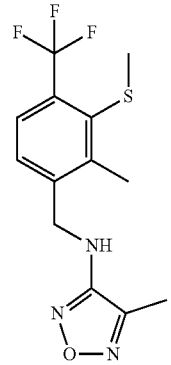 [SMILES: CSc1c(C(F)(F)F)ccc(CNc2nonc2C)c1C]

Sodium borohydride (30 mg, 0.793 mmol) was added to a solution of 1-[2-methyl-3-methylsulfanyl-4-(trifluoromethyl)phenyl]-N-(4-methyl-1,2,5-oxadiazol-3-yl)methanimine 46 (100 mg, 0.317 mmol) in methanol (3 mL) and the mixture was stirred at room temperature for 1.5 h. Water (10 mL) and ethyl acetate (10 mL) were added and the aqueous layer was further extracted with ethyl acetate (2×15 mL). The combined organic phases were dried (MgSO$_4$), filtered and concentrated to give the crude product which was purified by flash chromatography on silica gel (solvent 20% EtOAc/hexane) to afford the title compound as a colourless oil (77 mg, 76%).

$^1$H NMR $\delta_H$ (300 MHz, CDCl$_3$); 7.61 (d, J=9.0 Hz, 1H), 7.44 (d, J=9.0 Hz, 1H), 4.59 (d, J=6 Hz, 2H), 3.92 (br s, 1H), 2.72 (s, 3H), 2.30 (s, 6H); ESI-MS 318.0 [MH$^+$].

2-Methyl-N-(4-methyl-1,2,5-oxadiazol-3-yl)-3-methylsulfanyl-4-(trifluoromethyl)benzamide 48

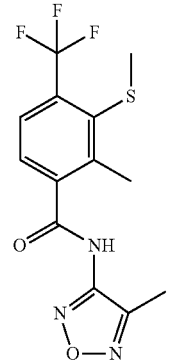 [SMILES: CSc1c(C(F)(F)F)ccc(C(=O)Nc2nonc2C)c1C]

Oxalyl chloride (120 µL, 1.20 mmol) was added to a solution of 2-methyl-3-methylsulfanyl-4-(trifluoromethyl)benzoic acid (200 mg, 0.80 mmol) and N,N-dimethylformamide (2 drops) in dichloromethane (3.5 mL) and the mixture was stirred at room temperature for 2 h.

Concentration under reduced pressure gave the crude acid chloride (0.80 mmol), which was used without further purification.

Sodium bis(trimethylsilyl)amide (1M solution in tetrahydrofuran, 1.2 mL, 1.20 mmol) was added to a solution of 4-methyl-1,2,5-oxadiazol-3-amine (95 mg, 96 mmol) in tetrahydrofuran (2 mL) at −78° C. and the mixture was stirred at that temperature for 1 h. The mixture was gradually allowed to warm to −30° C. and a solution of the acid chloride (0.8 mmol) in tetrahydrofuran (2 mL) was added. The mixture was allowed to warm to room temperature and was stirred for 16 h. Saturated ammonium chloride solution (10 mL) and ethyl acetate (10 mL) were added, the organic layer separated and the aqueous layer further extracted with ethyl acetate (2×15 mL). The combined organic phases were dried (MgSO$_4$), filtered and concentrated to give the crude product which was purified by flash chromatography on silica gel (solvent 33% Et$_2$O/hexane) to afford the title compound as a colourless oil (84 mg, 32%).

$^1$H NMR δ$_H$ (300 MHz, CDCl$_3$); 7.78 (br s, 1H), 7.56 (d, J=8.0 Hz, 1H), 7.44 (d, J=8.0 Hz, 1H), 2.65 (s, 3H), 2.35 (s, 3H), 2.16 (s, 3H); ESI-MS 354.0 [MNa$^+$].

Compound 48 forms part of the prior art (WO2011/035874) and is included for reference purposes only.

Example 6—Testing the Herbicidal Activity of Compounds of the Invention

Compounds 22, 23 and 24 were screened for herbicidal efficacy against target plants: garden cress, *Lepidium sativum*, common chickweed, *Stellaria media*, and white mustard *Sinapsis alba*

Test Systems

Plants were obtained as seeds and were grown to the 2-4 true leaf stage. Plants were grown under laboratory conditions, individually in seed trays. Each plant (in an approximately 3 cm diameter plug) was then detached from the tray for spraying.

Environmental conditions were closely monitored and recorded and were within the optimal range of the target species.

Test Treatments and Application

The compounds were screened at a range of five concentrations, diluted in acetone and Tween™. A carrier only control was also conducted. Treatments were applied directly onto the plants, using a potter tower, at a specified application rate.

Experimental Design

One plant of each species was sprayed using a potter tower. The 3 different types of plants were placed on a 10 cm diameter platform directly beneath the potter sprayer and sprayed simultaneously. The growth of the plants and any Phytotoxicity effects were then assessed at intervals over 21 days, according to EPPO guideline PP1/135.

Five replicas were performed for each treatment, for each species.

In the tables below C represents a percentage increase in necrosis relative to the control of 0.1-50; B represents a percentage inhibition of 50-80; and A represents a percentage inhibition of 80-100.

TABLE 1A

Chickweed

Average of necrosis

| Compound | Dose g/ha | 1 | 2 | 3 | 4 | 5 | 7 | 10 | 14 |
|---|---|---|---|---|---|---|---|---|---|
| 22 | 200 | C | C | C | B | A | A | A | |
|  | 100 | C | C | C | B | A | A | A | |
|  | 50 | C | C | C | B | B | B | A | |
|  | 25 | C | C | C | C | A | A | A | |
|  | 12.5 | C | C | C | C | B | B | B | |
| 23 | 200 | C | C | C | C | B | B | B | |
|  | 100 | C | C | C | C | B | B | A | |
|  | 50 | C | C | C | C | B | B | B | |
|  | 25 | C | C | C | C | B | B | B | |
|  | 12.5 | C | C | C | C | B | B | A | |
| 24 | 200 | C | C | C | C | A | A | A | |
|  | 100 | C | C | C | B | B | B | A | |
|  | 50 | C | C | C | C | A | A | A | |
|  | 25 | C | C | C | C | C | C | C | |
|  | 12.5 | C | C | C | C | C | C | C | |
| untreated | 0 | C | C | C | C | C | C | C | C |

TABLE 1B

Garden Cress

Average of necrosis

| Compound | Dose g/ha | 1 | 2 | 3 | 4 | 5 | 7 | 10 | 14 |
|---|---|---|---|---|---|---|---|---|---|
| 22 | 200 | C | C | C | C | B | B | A | |
|  | 100 | C | C | C | C | B | B | B | |
|  | 50 | C | C | C | C | B | B | B | |
|  | 25 | C | C | C | C | C | C | A | |
|  | 12.5 | C | C | C | C | C | C | B | |
| 23 | 200 | C | B | B | B | B | B | B | |
|  | 100 | C | C | C | C | B | B | B | |
|  | 50 | C | C | C | C | B | B | B | |
|  | 25 | C | C | C | C | C | C | B | |
|  | 12.5 | C | C | C | C | C | C | C | |
| 24 | 200 | C | C | C | C | C | C | B | |
|  | 100 | C | C | C | B | B | B | B | |
|  | 50 | C | C | B | B | B | A | A | |
|  | 25 | C | C | C | C | C | C | C | |
|  | 12.5 | C | C | C | C | C | C | B | |
| untreated | 0 | C | C | C | C | C | C | C | C |

TABLE 1C

Mustard

Average of necrosis

| Compound | Dose g/ha | 1 | 2 | 3 | 4 | 5 | 7 | 10 | 14 |
|---|---|---|---|---|---|---|---|---|---|
| 22 | 200 | C | C | C | C | C | C | B | |
|  | 100 | C | C | C | C | C | C | B | |
|  | 50 | C | C | C | C | B | B | B | |
|  | 25 | C | C | C | C | C | C | C | |
|  | 12.5 | C | C | C | C | C | C | B | |
| 23 | 200 | C | C | C | C | C | C | C | |
|  | 100 | C | C | C | C | C | C | C | |
|  | 50 | C | C | C | C | C | C | C | |
|  | 25 | C | C | C | C | C | C | C | |
|  | 12.5 | C | C | C | C | C | C | C | |
| 24 | 200 | C | C | C | C | C | C | C | |
|  | 100 | C | C | C | C | C | C | C | |
|  | 50 | C | C | C | C | C | C | C | |
|  | 25 | C | C | C | C | C | C | C | |
|  | 12.5 | C | C | C | C | C | C | C | |
| untreated | 0 | C | C | C | C | C | C | C | C |

Certain compounds of the invention were screened for herbicidal efficacy against target plants: *Amaranthus retroflexus* (redroot pigweed), *Abutilon theophrasti* (China Jute): *Capsella bursa-pastoris*, (shepherd's-purse) *Echinochloa crus-galli*, *Hordeum vulgare* (Barley),

TABLE 2

| | Average of corrected necrosis | | | | | | | |
|---|---|---|---|---|---|---|---|---|
| | Compound | | | | | | | |
| | 25 | | 22 | | 24 | | 26 | |
| | Days post application | | | | | | | |
| | 1 | 7 | 1 | 7 | 1 | 7 | 1 | 7 |
| *A. retroflexus* | | | | | | | | |
| 6.25 g/ha | C | A | C | A | C | A | C | A |
| 12.5 | C | A | C | A | C | A | C | A |
| 25 | C | A | C | A | C | A | C | A |
| 50 | C | A | C | A | C | A | C | A |
| 100 | C | A | C | A | C | A | C | A |
| *A. theophrasti* | | | | | | | | |
| 6.25 | C | A | C | A | 0 | A | C | A |
| 12.5 | C | A | C | A | 0 | A | 0 | A |

TABLE 2-continued

| | Average of corrected necrosis | | | | | | | |
|---|---|---|---|---|---|---|---|---|
| | Compound | | | | | | | |
| | 25 | | 22 | | 24 | | 26 | |
| | Days post application | | | | | | | |
| | 1 | 7 | 1 | 7 | 1 | 7 | 1 | 7 |
| 25 | C | A | C | A | 0 | A | C | A |
| 50 | C | A | C | A | 0 | A | C | A |
| 100 | C | A | C | A | C | A | B | A |
| *C. bursa pastoris* | | | | | | | | |
| 6.25 | 0 | A | 0 | A | C | A | C | A |
| 12.5 | 0 | A | C | A | 0 | B | C | 0 |
| 25 | 0 | A | C | A | C | A | C | A |
| 50 | C | A | 0 | A | C | A | C | A |
| 100 | C | A | C | A | C | A | C | A |

All compounds for which the data is presented in table 2 showed excellent control over all target weed species after 7 days. Indeed, compound 26 showed better control than the reference compound (saflufenacil), against certain weed species after 1 day indicating that it is faster acting.

TABLE 3

| | Average of % corrected necrosis | | | | | | | | | | | | | | | |
|---|---|---|---|---|---|---|---|---|---|---|---|---|---|---|---|---|
| | Compound | | | | | | | | | | | | | | | |
| | 34 | | | | 27 | | | | 37 | | | 27a | | | 30 | |
| | Days after application | | | | | | | | | | | | | | | |
| | 1 | 4 | 10 | 16 | 1 | 4 | 10 | 16 | 4 | 7 | 10 | 4 | 7 | 10 | 4 | 7 | 10 |
| *A. theophrasti* | | | | | | | | | | | | | | | | | |
| 10 | 0 | C | C | C | 0 | C | C | C | | | | | | | | | |
| 20 | 0 | C | C | C | 0 | C | 0 | 0 | C | C | C | C | B | B | C | C | B |
| 40 | C | C | C | C | C | C | 0 | 0 | C | B | B | C | C | C | C | C | C |
| 80 | C | C | C | C | C | C | 0 | 0 | B | A | A | C | B | B | 0 | C | C |
| 160 | C | C | C | C | C | C | C | 0 | C | C | C | C | B | B | C | B | B |
| *E. crus galli* | | | | | | | | | | | | | | | | | |
| 10 | C | C | C | C | 0 | 0 | C | C | | | | | | | | | |
| 20 | C | C | C | C | 0 | C | 0 | 0 | C | C | C | C | C | C | 0 | C | 0 |
| 40 | C | C | C | C | 0 | 0 | 0 | 0 | B | B | B | B | B | B | 0 | C | C |
| 80 | 0 | C | C | C | 0 | 0 | 0 | C | A | A | A | C | C | C | 0 | 0 | 0 |
| 160 | 0 | C | C | C | C | C | C | C | B | B | A | C | C | C | C | C | C |
| *H. vulgare* | | | | | | | | | | | | | | | | | |
| 10 | 0 | C | C | C | 0 | 0 | C | C | | | | | | | | | |
| 20 | 0 | C | C | C | 0 | 0 | 0 | 0 | C | C | C | C | C | C | C | C | C |
| 40 | 0 | C | C | C | 0 | C | 0 | 0 | C | C | C | C | C | C | 0 | 0 | C |
| 80 | 0 | C | C | C | 0 | 0 | 0 | 0 | C | A | A | C | C | C | 0 | 0 | C |
| 160 | 0 | C | C | C | 0 | C | C | C | C | C | B | 0 | B | B | C | C | C |

| | Compound | | | | | | | | | | | | | | |
|---|---|---|---|---|---|---|---|---|---|---|---|---|---|---|---|
| | 28 | | | 35 | | | 29 | | | 39 | | | 38 | | |
| | Days after application | | | | | | | | | | | | | | |
| | 4 | 7 | 10 | 4 | 7 | 10 | 4 | 7 | 10 | 4 | 7 | 10 | 4 | 7 | 10 |
| *A. theophrasti* | | | | | | | | | | | | | | | |
| 10 | | | | | | | | | | | | | | | |
| 20 | C | C | C | C | C | C | 0 | C | A | C | C | C | C | B | B |
| 40 | C | B | B | C | C | C | C | C | B | C | C | B | C | C | C |
| 80 | C | C | C | C | C | C | C | C | B | C | C | B | C | C | C |
| 160 | C | C | B | C | C | C | C | C | B | C | B | A | C | C | B |
| *E. crus galli* | | | | | | | | | | | | | | | |
| 10 | | | | | | | | | | | | | | | |
| 20 | C | C | C | 0 | C | C | 0 | C | C | C | 0 | C | C | 0 | 0 |

TABLE 3-continued

| | | | | | Average of % corrected necrosis | | | | | | | | | | |
|---|---|---|---|---|---|---|---|---|---|---|---|---|---|---|---|
| 40 | B | C | C | 0 | 0 | 0 | C | C | C | 0 | B | B | C | B | B |
| 80 | 0 | C | C | 0 | 0 | 0 | C | C | C | 0 | 0 | 0 | C | B | B |
| 160 | C | C | C | 0 | C | C | C | C | B | C | C | C | C | C | C |
| *H. vulgare* | | | | | | | | | | | | | | | |
| 10 | | | | | | | | | | | | | | | |
| 20 | 0 | C | C | 0 | C | C | 0 | B | B | 0 | 0 | 0 | 0 | 0 | 0 |
| 40 | 0 | C | C | 0 | 0 | 0 | 0 | C | C | 0 | 0 | C | 0 | C | C |
| 80 | 0 | 0 | 0 | 0 | 0 | 0 | 0 | C | C | 0 | 0 | 0 | 0 | C | C |
| 160 | 0 | C | C | 0 | 0 | 0 | 0 | C | C | 0 | C | 0 | 0 | C | C |

All compounds for which the data is presented in table 3 showed activity against all target weed species.

In particular, compound 37 showed excellent control over all three weed species. Indeed, compound 37 showed significantly better control than prior art compounds with known activity (compound 27 and 27a)

TABLE 4

| | | | | Average of % corrected necrosis | | | | | | | |
|---|---|---|---|---|---|---|---|---|---|---|---|
| | | | | Compound | | | | | | | |
| | 49 | | | | 42 | | | | 43 | | |
| | Days after application | | | | | | | | | | |
| | 1 | 4 | 10 | 16 | 1 | 4 | 10 | 16 | 1 | 4 | 10 | 16 |
| *A. theophrasti* | | | | | | | | | | | | |
| 10 | C | C | C | C | C | C | 0 | 0 | C | C | B | B |
| 20 | C | C | C | C | C | C | C | C | C | C | C | C |
| 40 | C | 0 | C | C | 0 | 0 | C | C | C | C | C | C |
| 80 | C | 0 | C | C | 0 | C | C | C | C | C | 0 | 0 |
| 160 | 0 | C | 0 | C | 0 | C | C | C | C | C | 0 | 0 |
| *E. crus galli* | | | | | | | | | | | | |
| 10 | 0 | C | C | C | C | 0 | C | 0 | 0 | C | C | C |
| 20 | 0 | 0 | 0 | 0 | 0 | C | C | C | C | C | 0 | 0 |
| 40 | C | 0 | C | C | C | C | C | C | 0 | C | 0 | 0 |
| 80 | 0 | 0 | C | C | C | C | C | C | C | 0 | 0 | 0 |
| 160 | 0 | C | 0 | 0 | 0 | C | C | C | 0 | C | 0 | 0 |
| *H. vulgare* | | | | | | | | | | | | |
| 10 | 0 | 0 | C | C | 0 | 0 | 0 | 0 | C | C | C | |
| 20 | 0 | 0 | C | C | 0 | 0 | 0 | C | 0 | 0 | 0 | |
| 40 | 0 | 0 | C | C | 0 | C | C | 0 | 0 | 0 | 0 | |
| 80 | 0 | 0 | C | C | 0 | C | C | 0 | 0 | 0 | 0 | |
| 160 | 0 | 0 | 0 | 0 | 0 | 0 | C | C | 0 | C | 0 | 0 |

All compounds for which the data is presented in table 4 showed activity against all target weed species.

Compound 49 forms part of the prior art (WO2013/017559) and is included as a reference only:

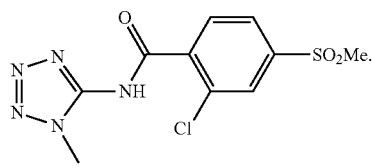

49

TABLE 5

| | | Average of % corrected necrosis | | | | | | | |
|---|---|---|---|---|---|---|---|---|---|
| | | Compound | | | | | | | |
| | 47 | | | 46 | | | 48 | | |
| | Days after application | | | | | | | | |
| | 4 | 7 | 10 | 4 | 7 | 10 | 4 | 7 | 10 |
| *A. theophrasti* | | | | | | | | | |
| 6.25 | | | | C | C | C | C | C | B |
| 12.5 | C | C | A | C | C | C | C | C | B |
| 25 | C | C | B | C | C | B | C | C | B |
| 50 | C | C | B | C | C | B | C | C | B |
| 100 | C | B | B | B | B | B | C | B | B |
| *E. crus galli* | | | | | | | | | |
| 6.25 | | | | C | C | C | C | C | C |
| 12.5 | C | C | B | C | C | C | C | C | C |
| 25 | C | C | B | 0 | 0 | C | C | C | C |
| 50 | C | C | B | C | C | C | C | C | C |
| 100 | C | C | B | B | B | A | C | B | B |
| *H. vulgare* | | | | | | | | | |
| 6.25 | | | | 0 | 0 | 0 | 0 | C | C |
| 12.5 | C | C | C | 0 | 0 | 0 | C | C | C |
| 25 | C | C | B | 0 | C | C | C | C | C |
| 50 | C | C | B | C | C | C | 0 | C | C |
| 100 | C | C | B | C | C | C | 0 | C | A |

All compounds for which the data is presented in Table 5 showed activity against all tested weed species. Both compound 47 and 48 showed good control over *A. theophrasti* and *E. crus galli* after 10 days, with compound 47 also showing good control over *H. vulgare*. Indeed, compound 47 showed improved control of *E. crus galli* and *H. vulgare* at low dosages relative to the reference compound 48, a compound with known activity.

The invention claimed is:
1. A compound of formula I:

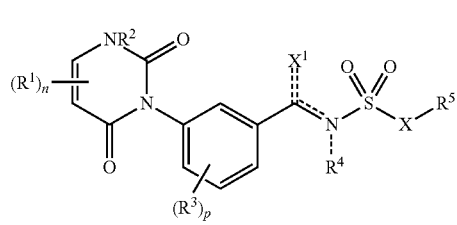

I wherein
===== represents a single bond or a double bond;
X is $CR^7R^7$;
===== $X^1$ is selected from: $=O$, $—R^7$ or $(—R^7)_2$;

$R^1$ and $R^3$ are each independently at each occurrence selected from $C_1$-$C_4$ alkyl, $C_1$-$C_4$-haloalkyl, halogen, nitro, $OR^8$, $SR^8$, cyano, $C_2$-$C_4$ alkenyl, $C_2$-$C_4$ alkynyl, $C_3$-$C_6$ cycloalkyl and $NR^8R^8$;

$R^2$ and $R^6$ are each independently selected from: H, $C_1$-$C_4$ alkyl, $C_3$-$C_6$-cycloalkyl and $C_1$-$C_4$ haloalkyl;

$R^4$ is absent or is independently selected from: H, $C_1$-$C_4$ alkyl, $C_3$-$C_6$-cycloalkyl and $C_1$-$C_4$ haloalkyl;

$R^5$ is independently selected from $C_1$-$C_4$ alkyl, $C_3$-$C_6$-cycloalkyl and $C_1$-$C_4$ haloalkyl;

$R^7$ is independently at each occurrence selected from: H, $C_1$-$C_4$ alkyl, $C_3$-$C_6$-cycloalkyl and $C_1$-$C_4$ haloalkyl;

$R^8$ is independently at each occurrence selected from; H, $C_1$-$C_4$ alkyl, $C(O)$—$C_1$-$C_4$-alkyl and $C_1$-$C_4$ haloalkyl;

n is an integer selected from 0, 1 and 2;

p is an integer independently selected from 0, 1, 2 and 3;

wherein in any $R^1$-$R^8$ group which contains an alkyl, haloalkyl, cycloalkyl, heterocycloalkyl, aryl (including phenyl, biphenyl and naphthyl) or heteroaryl group, that alkyl, haloalkyl, cycloalkyl, heterocycloalkyl, aryl or heteroaryl group is optionally substituted, where chemically possible, by 1 to 4 substituents which are each independently selected at each occurrence from the group consisting of: oxo; $=NR^a$; $=NOR^a$; $R^a$; halo; nitro; cyano; $NR^aR^a$; $SO_3R^a$; $SO_2R^a$; $SO_2NR^aR^a$; $CO_2R^a$; $C(O)R^a$; $CONR^aR^a$; $CH_2NR^aR^a$; $CH_2OR^a$ and $OR^a$;

wherein $R^a$ is selected from H, $C_1$-$C_4$ alkyl and $C_1$-$C_4$ haloalkyl; and wherein, in the case of an aryl group or heteroaryl group, any two of these substituents (e.g. $NR^aR^a$, $OR^a$, $SR^a$, $R^a$) when present on neighbouring atoms in the aryl or heteroaryl group may, where chemically possible, together with the atoms to which they are attached form a ring which is fused to the aryl or heteroaryl group;

or an agronomically acceptable salt or N-oxide thereof.

2. The compound of claim 1, wherein the compound is a compound of formula II:

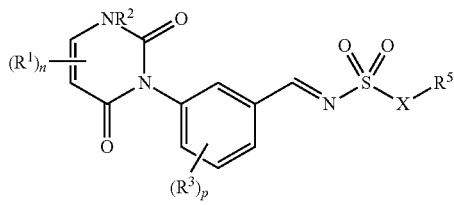

and wherein $R^1$, $R^2$, $R^3$, $R^5$, X, n and p are as defined in claim 1.

3. The compound of claim 1, wherein the compound is a compound of formula IV:

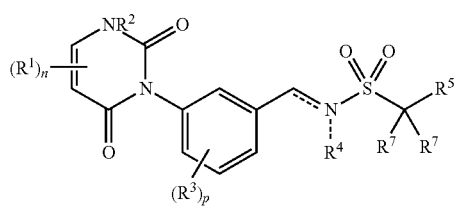

and wherein $R^1$, $R^2$, $R^3$, $R^5$, $R^4$, $R^7$, n and p are as defined in claim 1.

4. The compound of claim 1, wherein the compound is a compound of formula VII:

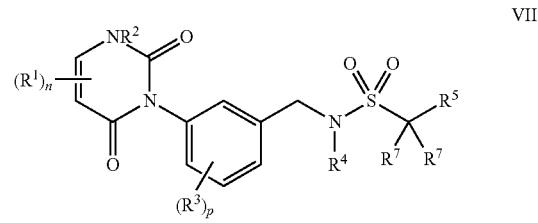

wherein $R^4$ is independently selected from: H, $C_1$-$C_4$ alkyl, $C_3$-$C_6$-cycloalkyl and $C_1$-$C_4$ haloalkyl, and wherein $R^1$, $R^2$, $R^3$, $R^5$, $R^7$, n and p are as defined in claim 1.

5. The compound of claim 1, wherein the compound is a compound of formula XXIX:

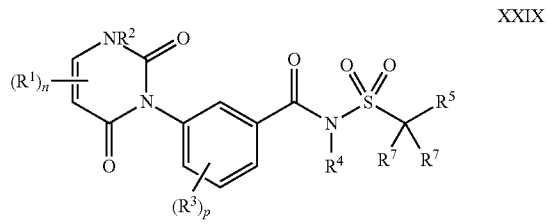

and wherein $R^4$ is independently selected from: H, $C_1$-$C_4$ alkyl, $C_3$-$C_6$-cycloalkyl and $C_1$-$C_4$ haloalkyl, and wherein $R^1$, $R^2$, $R^3$, $R^5$, $R^7$, n and p are as defined in claim 1.

6. The compound of claim 1, wherein n is 1.

7. The compound of claim 1, wherein $R^3$ is independently selected from: $C_1$-$C_4$ alkyl, $C_1$-$C_4$-haloalkyl, halogen and $C_3$-$C_6$ cycloalkyl.

8. The compound of claim 1, wherein $R^2$ is selected from: $C_1$-$C_4$ alkyl, $C_3$-$C_6$-cycloalkyl and $C_1$-$C_4$ haloalkyl.

9. The compound of claim 1, wherein $R^4$ is H.

10. The compound of claim 1, wherein $R^5$ is $C_1$-$C_4$ alkyl.

11. A method for controlling weeds, the method comprising applying an agronomically effective quantity of a compound of claim 1 to the plants themselves or to the area where it is intended that the plants will grow, wherein the quantity of the compound of claim 1 is substantially non-phytotoxic to the crop plant.

12. A herbicidal composition comprising an effective amount of an active compound of claim 1.

13. The compound of claim 1, wherein the compound is selected from:

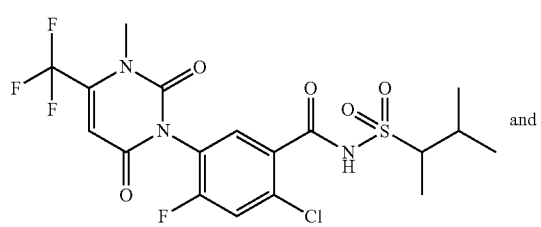

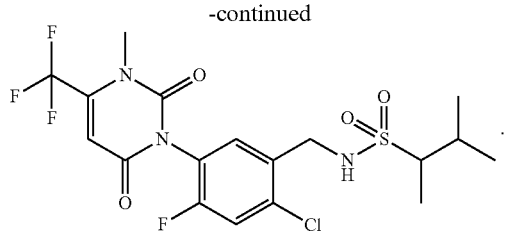
14. The compound of claim 1, wherein the compound is:
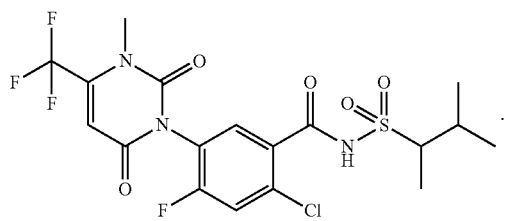 [SMILES: CC(C)C(C)S(=O)(=O)NC(=O)c1cc(-n2c(=O)cc(C(F)(F)F)n(C)c2=O)c(F)cc1Cl]
15. The compound of claim 6, wherein $R^1$ is selected from: $C_1$-$C_4$ alkyl, $C_1$-$C_4$-haloalkyl, halogen and $C_3$-$C_6$ cycloalkyl.
* * * * *